US012738020B2

(12) United States Patent
Hiasa

(10) Patent No.: US 12,738,020 B2
(45) Date of Patent: Sep. 15, 2026

(54) IMAGE PROCESSING DEVICE, CORRECT ANSWER DATA GENERATION DEVICE, SIMILAR IMAGE SEARCH DEVICE, IMAGE PROCESSING METHOD, AND PROGRAM

(71) Applicant: FUJIFILM Corporation, Tokyo (JP)

(72) Inventor: Yuta Hiasa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 282 days.

(21) Appl. No.: 18/395,714

(22) Filed: Dec. 25, 2023

(65) Prior Publication Data

US 2024/0127578 A1 Apr. 18, 2024

Related U.S. Application Data

(63) Continuation of application No. PCT/JP2022/024947, filed on Jun. 22, 2022.

(30) Foreign Application Priority Data

Jun. 29, 2021 (JP) ................................ 2021-107710
May 24, 2022 (JP) ................................ 2022-084433

(51) Int. Cl.
*G06V 10/00* (2022.01)
*G06V 10/25* (2022.01)
(Continued)

(52) U.S. Cl.
CPC ............ *G06V 10/761* (2022.01); *G06V 10/25* (2022.01); *G06V 10/44* (2022.01); *G06V 10/54* (2022.01);
(Continued)

(58) Field of Classification Search
CPC ...... G06V 10/761; G06V 10/25; G06V 10/44; G06V 10/54; G06V 2201/03;
(Continued)

(56) References Cited

U.S. PATENT DOCUMENTS

2013/0251099 A1* 9/2013 Kunz .................. A61B 5/0036 378/65
2014/0072196 A1* 3/2014 Hwang ................ G06T 7/0016 382/130

(Continued)

FOREIGN PATENT DOCUMENTS

| CN | 111768394 | 10/2020 |
|---|---|---|
| CN | 112150419 | 12/2020 |
| JP | 2021512671 | 5/2021 |

OTHER PUBLICATIONS

Zhou et al., "Anatomy guided Multimodal Registration by Learning Segmentation without Ground Truth: Application to Intraprocedural CBCT/MR Liver Segmentation and Registration", Medical Image Analysis, Sep. 2020, pp. 1-13. (Year: 2020).*

(Continued)

*Primary Examiner* — Van D Huynh
(74) *Attorney, Agent, or Firm* — JCIPRNET

(57) ABSTRACT

An image processing device 10 includes a processor 12, and the processor 12 is configured to execute an image acquisition process of acquiring a first image in a first image space and a second image in a second image space different from the first image space, a first conversion process of converting the first image into an image in a third image space that is characterized by a region of interest, using a first converter, a second conversion process of converting the second image into an image in the third image space using a second converter, and a first similarity calculation process of calculating a first similarity between the first image and the second image in the third image space.

36 Claims, 18 Drawing Sheets

(51) Int. Cl.

| | |
|---|---|
| ***G06V 10/44*** | (2022.01) |
| ***G06V 10/54*** | (2022.01) |
| ***G06V 10/74*** | (2022.01) |
| ***G16H 50/20*** | (2018.01) |

(52) U.S. Cl.

CPC ......... *G16H 50/20* (2018.01); *G06V 2201/03* (2022.01)

(58) Field of Classification Search

CPC .. G06V 2201/031; G16H 50/20; A61B 6/032; A61B 6/5205; A61B 6/5217; A61B 6/5235; G06T 7/00; G06T 7/33

See application file for complete search history.

(56) References Cited

U.S. PATENT DOCUMENTS

| | | | | |
|---|---|---|---|---|
| 2017/0148180 | A1* | 5/2017 | Elenbaas | G06T 7/30 |
| 2018/0330511 | A1 | 11/2018 | Ha et al. | |
| 2021/0109181 | A1 | 4/2021 | Beck et al. | |
| 2023/0087494 | A1* | 3/2023 | Vilsmeier | G06V 40/10 382/159 |

OTHER PUBLICATIONS

M. D. Ketcha et al., "Automatic Masking for Robust 3D-2D Image Registration in Image-Guided Spine Surgery", Proceedings of SPIE—the International Society for Optical Engineering, Mar. 18, 2016, pp. 1-7, vol. 9786.

Takehito Hayami et al., "Super High Dynamic Range Imaging", 2014 22nd International Conference on Pattern Recognition, Aug. 24, 2014, pp. 720-725.

P. Markelj et al., "A review of 3D/20 registration methods for image-guided interventions", Medical Image Analysis, Apr. 13, 2010, pp. 642-661, vol. 16, No. 3.

"Search Report of Europe Counterpart Application", issued on Sep. 13, 2024, p. 1-p. 9.

"International Search Report (Form PCT/ISA/210) of PCT/JP2022/024947", mailed on Sep. 13, 2022, with English translation thereof, pp. 1-4.

"Written Opinion of the International Searching Authority (Form PCT/ISA/237) of PCT/JP2022/024947", mailed on Sep. 13, 2022, with English translation thereof, pp. 1-6.

Martin Simonovsky et al., "A Deep Metric for Multimodal Registration", Conference: International Conference on Medical Image Computing and Computer-Assisted Intervention, Oct. 2016, pp. 10-18.

Daniel Toth et al., "3D/2Dmodel-to-image registration by imitation learning for cardiac procedures", International Journal of Computer Assisted Radiology and Surgery, May 2018, pp. 1141-1149.

Bo Zhou et al., "Anatomy-guided Multimodal Registration by Learning Segmentation without Ground Truth: Application to Intraprocedural CBCT/MR Liver Segmentation and Registration", Medical Image Analysis, Sep. 2020, pp. 1-13.

Moab Arar et al., "Unsupervised Multi-Modal Image Registration via Geometry Preserving Image-to-Image Translation", 2020 IEEE/CVF Conference on Computer Vision and Pattern Recognition (CVPR), Jun. 2020, pp. 13410-13419.

* cited by examiner 104A
104B
104C
104D
16
FIRST CONVERTER
102

106
108
18
SECOND CONVERTER
GEOMETRY
40
REGISTRATION PARAMETER θ
42
110A
110B
110C
110D

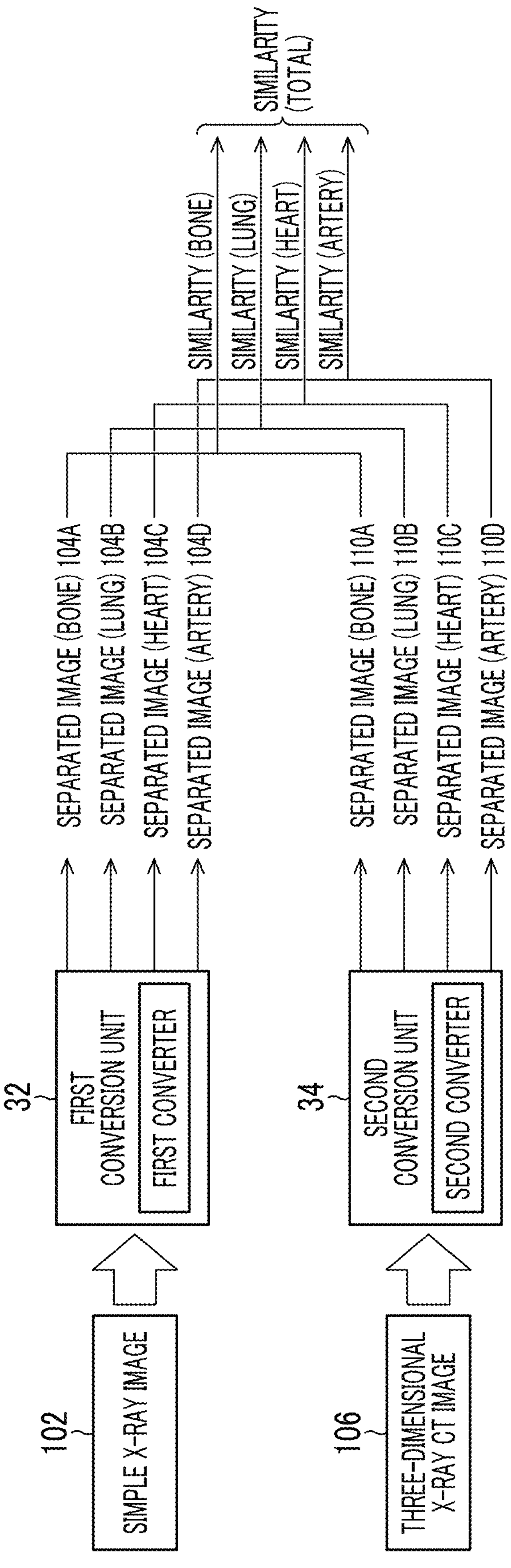
FIG. 6
102
SIMPLE X-RAY IMAGE
106
THREE-DIMENSIONAL X-RAY CT IMAGE
32
FIRST CONVERSION UNIT
FIRST CONVERTER
34
SECOND CONVERSION UNIT
SECOND CONVERTER
SEPARATED IMAGE (BONE) 104A
SEPARATED IMAGE (LUNG) 104B
SEPARATED IMAGE (HEART) 104C
SEPARATED IMAGE (ARTERY) 104D
SEPARATED IMAGE (BONE) 110A
SEPARATED IMAGE (LUNG) 110B
SEPARATED IMAGE (HEART) 110C
SEPARATED IMAGE (ARTERY) 110D
SIMILARITY (BONE)
SIMILARITY (LUNG)
SIMILARITY (HEART)
SIMILARITY (ARTERY)
SIMILARITY (TOTAL)

102
T
202
204
202A
204A
Q1
Q2

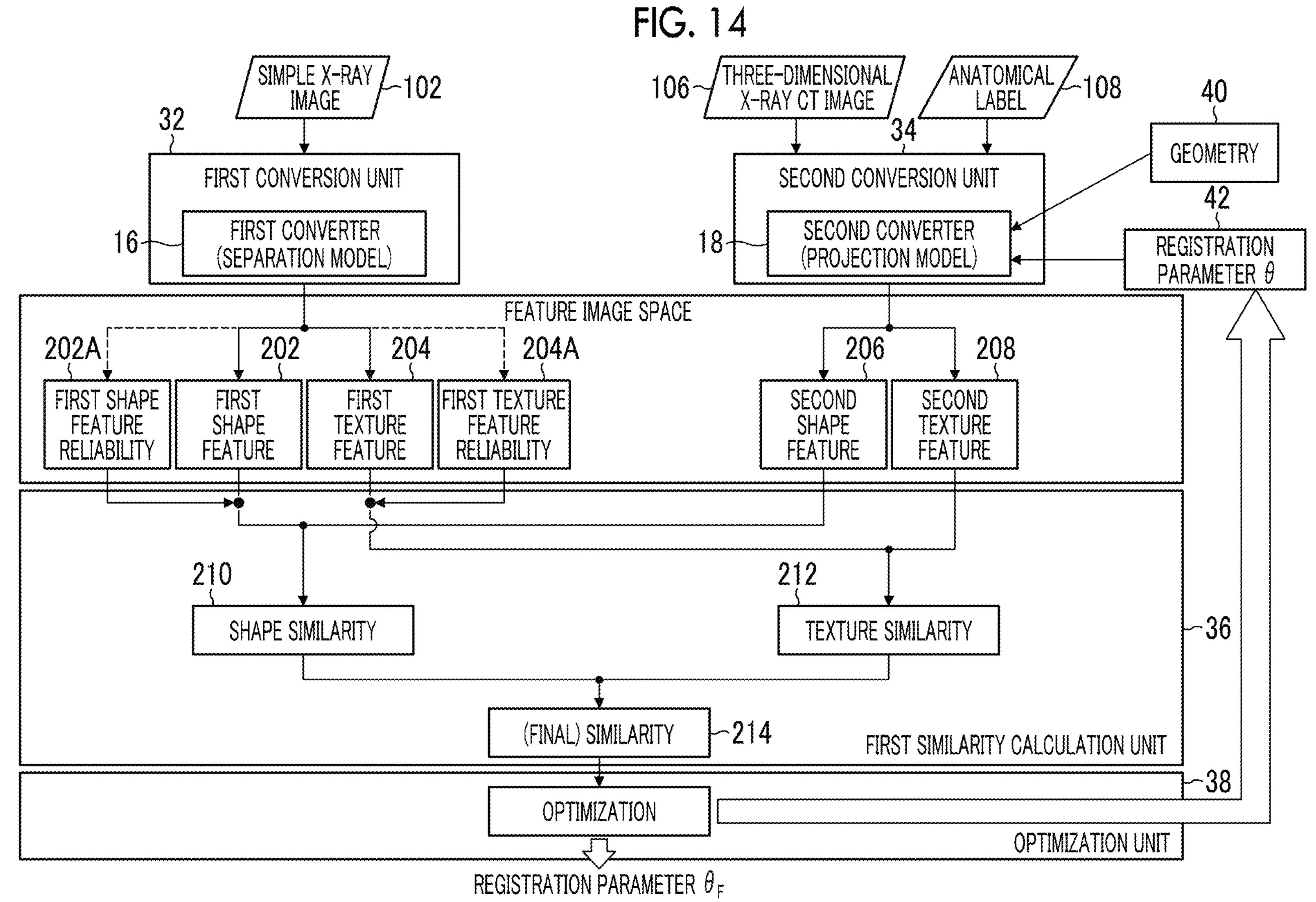
FIG. 14
SIMPLE X-RAY IMAGE
102
THREE-DIMENSIONAL X-RAY CT IMAGE
106
ANATOMICAL LABEL
108
40
GEOMETRY
32
FIRST CONVERSION UNIT
16
FIRST CONVERTER (SEPARATION MODEL)
34
SECOND CONVERSION UNIT
18
SECOND CONVERTER (PROJECTION MODEL)
42
REGISTRATION PARAMETER θ
FEATURE IMAGE SPACE
202A
FIRST SHAPE FEATURE RELIABILITY
202
FIRST SHAPE FEATURE
204
FIRST TEXTURE FEATURE
204A
FIRST TEXTURE FEATURE RELIABILITY
206
SECOND SHAPE FEATURE
208
SECOND TEXTURE FEATURE
210
SHAPE SIMILARITY
212
TEXTURE SIMILARITY
36
(FINAL) SIMILARITY
214
FIRST SIMILARITY CALCULATION UNIT
38
OPTIMIZATION
OPTIMIZATION UNIT
REGISTRATION PARAMETER θF

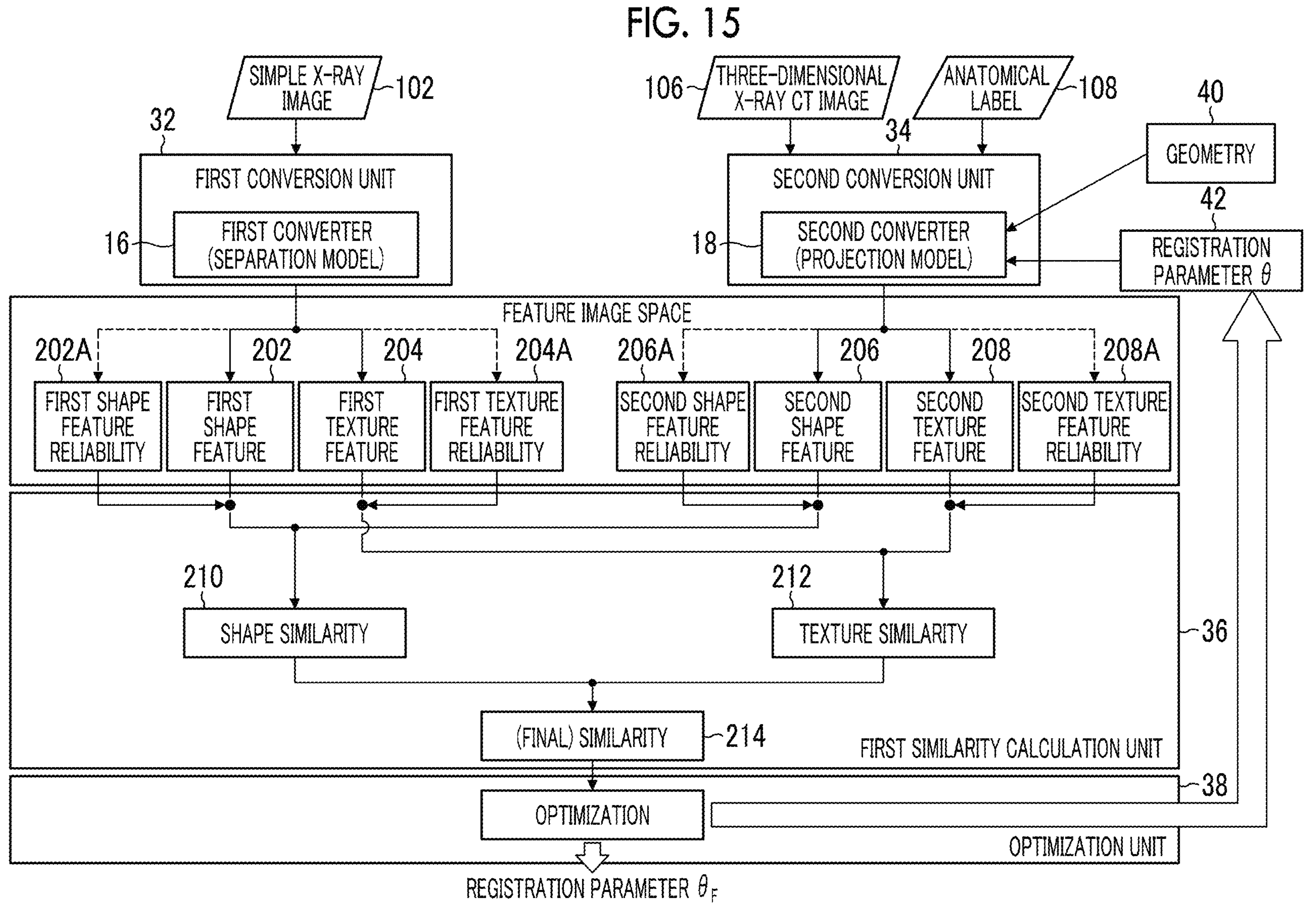
FIG. 15
SIMPLE X-RAY IMAGE
102
106
THREE-DIMENSIONAL X-RAY CT IMAGE
ANATOMICAL LABEL
108
40
GEOMETRY
32
FIRST CONVERSION UNIT
16
FIRST CONVERTER (SEPARATION MODEL)
34
SECOND CONVERSION UNIT
18
SECOND CONVERTER (PROJECTION MODEL)
42
REGISTRATION PARAMETER θ
FEATURE IMAGE SPACE
202A
202
204
204A
206A
206
208
208A
FIRST SHAPE FEATURE RELIABILITY
FIRST SHAPE FEATURE
FIRST TEXTURE FEATURE
FIRST TEXTURE FEATURE RELIABILITY
SECOND SHAPE FEATURE RELIABILITY
SECOND SHAPE FEATURE
SECOND TEXTURE FEATURE
SECOND TEXTURE FEATURE RELIABILITY
210
SHAPE SIMILARITY
212
TEXTURE SIMILARITY
36
(FINAL) SIMILARITY
214
FIRST SIMILARITY CALCULATION UNIT
38
OPTIMIZATION
OPTIMIZATION UNIT
REGISTRATION PARAMETER $\theta_F$

102
T
220
204
220A
204A
Q1
Q2
Q3

IMAGE PROCESSING DEVICE, CORRECT ANSWER DATA GENERATION DEVICE, SIMILAR IMAGE SEARCH DEVICE, IMAGE PROCESSING METHOD, AND PROGRAM

CROSS-REFERENCE TO RELATED APPLICATIONS

The present application is a Continuation of PCT International Application No. PCT/JP2022/024947 filed on Jun. 22, 2022 claiming priorities under 35 U.S.C § 119(a) to Japanese Patent Application No. 2021-107710 filed on Jun. 29, 2021 and Japanese Patent Application No. 2022-084433 filed on May 24, 2022. Each of the above applications is hereby expressly incorporated by reference, in its entirety, into the present application.

BACKGROUND OF THE INVENTION

1. Field of the Invention

The present invention is a technique related to an image processing device, a correct answer data generation device, a similar image search device, an image processing method, and a program.

2. Description of the Related Art

In the related art, registration between simple X-ray images has been often performed, using contrast-enhanced blood vessels, bones, implants, and the like as main targets, on the premise of clear features (for example, edges) in the images. However, in a case in which non-rigid registration of organs in a chest is performed using the simple X-ray images of the chest, it is not easy to calculate a similarity (cost function) specializing in soft tissues since bones are superimposed in the simple X-ray image in addition to the soft tissues.

In recent years, various proposals have been made for designing a similarity (designing a trained model for calculating the similarity). In metric learning which is one of techniques related to the design of the similarity, the similarity can be automatically designed by deep learning. For example, Simonovsky, Martin, et al. “A deep metric for multimodal registration.”, MICCAI, 2016. discloses metric learning in multimodal image registration. In addition, for example, Toth, Daniel, et al. “3D/2D model-to-image registration by imitation learning for cardiac procedures.”, IJCARS, 2018. discloses a three-dimensional model and metric learning in registration between two-dimensional images. Further, there is a method using monomodal conversion as another technique related to the design of the similarity. For example, Zhou, Bo, et al. “Anatomy-guided multimodal registration by learning segmentation without ground truth: Application to intra-procedural CBCT/MR liver segmentation and registration.”, Medical image analysis, 2021. discloses a technique related to conversion of an input image pair into a three-dimensional Euclidean space in multimodal image registration. Furthermore, for example, Arar, Moab, et al. “Unsupervised multi-modal image registration via geometry preserving image-to-image translation.”, CVPR, 2020. discloses a technique related to monomodal conversion in multimodal image registration.

SUMMARY OF THE INVENTION

However, the metric learning techniques disclosed in Simonovsky, Martin, et al. “A deep metric for multimodal registration.”, MICCAI, 2016. and Toth, Daniel, et al. “3D/2D model-to-image registration by imitation learning for cardiac procedures.”, IJCARS, 2018. have a problem that correct answer data after registration is required or interpretability is low. Further, the methods using monomodal conversion disclosed in Zhou, Bo, et al. “Anatomy-guided multimodal registration by learning segmentation without ground truth: Application to intra-procedural CBCT/MR liver segmentation and registration.”, Medical image analysis, 2021. and Arar, Moab, et al. “Unsupervised multi-modal image registration via geometry preserving image-to-image translation.”, CVPR, 2020. require the precondition that it is easy to design the similarity in the image space of either of the input images.

The present invention has been made in view of the above circumstances, and an object of the present invention is to provide an image processing device, a correct answer data generation device, a similar image search device, an image processing method, and a program that can easily calculate an interpretable similarity with high accuracy, without requiring correct answer data, even in a case in which it is not easy to design a similarity of an input image in an image space.

In order to achieve the object, according to an aspect of the present invention, there is provided an image processing device comprising a processor. The processor is configured to execute: an image acquisition process of acquiring a first image in a first image space and a second image in a second image space different from the first image space; a first conversion process of converting the first image into an image in a third image space that is characterized by a region of interest, using a first converter; a second conversion process of converting the second image into an image in the third image space using a second converter; and a first similarity calculation process of calculating a first similarity between the first image and the second image in the third image space.

According to this aspect, the first image and the second image are converted on the third image space characterized by the region of interest, and the similarity between the converted first image and second image is calculated. Therefore, in this aspect, even in a case in which it is not easy to design the similarity of the input image in the image space, it is possible to easily calculate an interpretable similarity with high accuracy, without requiring correct answer data.

Preferably, the first image is converted into images in a plurality of the third image spaces in the first conversion process. Preferably, in the second conversion process, the second image is converted into images in the plurality of third image spaces to correspond to the first conversion process. Preferably, in the first similarity calculation process, the first similarity in each of the plurality of third image spaces is calculated, and a plurality of the calculated first similarities are integrated.

Preferably, in the first conversion process, the first image is converted by at least two or more first converters into images in the third image spaces which correspond to each of the first converters. Preferably, in the second conversion process, the second image is converted by at least two or more second converters into images in the third image spaces, which correspond to each of the second converters, to correspond to the first conversion process.

Preferably, in the first similarity calculation process, the first similarity is calculated for each of the plurality of third image spaces.

Preferably, the region of interest is an anatomical region of interest, and the third image space is a feature image space characterized by the anatomical region of interest.

Preferably, the processor is configured to execute a region-of-interest receiving process of receiving an input of the region of interest, the first converter converts the first image on the third image space characterized by the region of interest received in the region-of-interest receiving process, and the second converter converts the second image on the third image space characterized by the region of interest received in the region-of-interest receiving process.

Preferably, the first converter outputs a first reliability indicating a reliability of the image after the conversion. Preferably, in the first similarity calculation process, the first similarity that has a weight or is to be selected is calculated on the basis of the first reliability.

Preferably, the first converter outputs the first reliability for each pixel of the image after the conversion.

Preferably, the first converter outputs a first reliability indicating a reliability of the image after the conversion, and the second converter outputs a second reliability indicating a reliability of the image after the conversion. Preferably, in the first similarity calculation process, the first similarity having a weight is calculated on the basis of the first reliability and the second reliability.

Preferably, the first converter outputs the first reliability for each pixel of the image after the conversion, and the second converter outputs the second reliability for each pixel of the image after the conversion.

Preferably, the first converter converts the first image into a first shape feature and a first texture feature, and the second converter converts the second image into a second shape feature and a second texture feature. Preferably, in the first similarity calculation process, the first similarity is calculated on the basis of a similarity between the first shape feature and the second shape feature and a similarity between the first texture feature and the second texture feature.

Preferably, the first converter outputs a (1-1)-th reliability indicating a reliability of the first shape feature and outputs a (1-2)-th reliability indicating a reliability of the first texture feature. Preferably, in the first similarity calculation process, a (1-1)-th similarity between the first shape feature and the second shape feature and a (1-2)-th similarity between the first texture feature and the second texture feature are calculated on the basis of the (1-1)-th reliability and the (1-2)-th reliability, and the first similarity is calculated.

Preferably, in the first similarity calculation process, the (1-1)-th similarity and the (1-2)-th similarity are weighted on the basis of the (1-1)-th reliability and the (1-2)-th reliability, and the first similarity is calculated.

Preferably, in the first similarity calculation process, the (1-1)-th similarity or the (1-2)-th similarity is selected on the basis of the (1-1)-th reliability and the (1-2)-th reliability, and the first similarity is calculated.

Preferably, the first converter outputs a (1-1)-th reliability indicating a reliability of the first shape feature and outputs a (1-2)-th reliability indicating a reliability of the first texture feature, and the second converter outputs a (2-1)-th reliability indicating a reliability of the second shape feature and outputs a (2-2)-th reliability indicating a reliability of the second texture feature. Preferably, in the first similarity calculation process, a (1-1)-th similarity between the first shape feature and the second shape feature and a (1-2)-th similarity between the first texture feature and the second texture feature are calculated on the basis of the (1-1)-th reliability, the (1-2)-th reliability, the (2-1)-th reliability, and the (2-2)-th reliability, and the first similarity is calculated.

Preferably, in the first similarity calculation process, the (1-1)-th similarity is weighted on the basis of the (1-1)-th reliability and the (2-1)-th reliability, the (1-2)-th similarity is weighted on the basis of the (1-2)-th reliability and the (2-2)-th reliability, and the first similarity is calculated.

Preferably, in the first similarity calculation process, the (1-1)-th similarity or the (1-2)-th similarity is selected on the basis of the (1-1)-th reliability, the (1-2)-th reliability, the (2-1)-th reliability, and the (2-2)-th reliability, and the first similarity is calculated.

Preferably, the first converter converts the first image into a first anatomical region and a first disease region, and the second converter converts the second image into a second anatomical region and a second disease region. Preferably, in the first similarity calculation process, the first similarity is calculated on the basis of a similarity between the first anatomical region and the second anatomical region and a similarity between the first disease region and the second disease region.

Preferably, the first converter outputs a (1-1)-th reliability indicating a reliability of the first anatomical region and outputs a (1-2)-th reliability indicating a reliability of the first disease region. Preferably, in the first similarity calculation process, a (1-1)-th similarity between the first anatomical region and the second anatomical region and a (1-2)-th similarity between the first disease region and the second disease region are calculated on the basis of the (1-1)-th reliability and the (1-2)-th reliability, and the first similarity is calculated.

Preferably, in the first similarity calculation process, the (1-1)-th similarity and the (1-2)-th similarity are weighted on the basis of the (1-1)-th reliability and the (1-2)-th reliability, and the first similarity is calculated.

Preferably, in the first similarity calculation process, the (1-1)-th similarity or the (1-2)-th similarity is selected on the basis of the (1-1)-th reliability and the (1-2)-th reliability, and the first similarity is calculated.

Preferably, the first converter outputs a (1-1)-th reliability indicating a reliability of the first anatomical region and outputs a (1-2)-th reliability indicating a reliability of the first disease region, and the second converter outputs a (2-1)-th reliability indicating a reliability of the second anatomical region and outputs a (2-2)-th reliability indicating a reliability of the second disease region. Preferably, in the first similarity calculation process, a (1-1)-th similarity between the first anatomical region and the second anatomical region and a (1-2)-th similarity between the first disease region and the second disease region are calculated on the basis of the (1-1)-th reliability, the (1-2)-th reliability, the (2-1)-th reliability, and the (2-2)-th reliability, and the first similarity is calculated.

Preferably, in the first similarity calculation process, the (1-1)-th similarity is weighted on the basis of the (1-1)-th reliability and the (2-1)-th reliability, the (1-2)-th similarity is weighted on the basis of the (1-2)-th reliability and the (2-2)-th reliability, and the first similarity is calculated.

Preferably, in the first similarity calculation process, the (1-1)-th similarity or the (1-2)-th similarity is selected on the basis of the (1-1)-th reliability, the (1-2)-th reliability, the (2-1)-th reliability, and the (2-2)-th reliability, and the first similarity is calculated.

Preferably, the processor is configured to execute a second similarity calculation process of calculating a second similarity between the first image and the second image. Preferably, in the first similarity calculation process, the first similarity weighted on the basis of the second similarity is calculated.

Preferably, the second similarity is an amount of mutual information between a simple X-ray image and a pseudo X-ray image generated from a three-dimensional X-ray CT image.

Preferably, the second similarity is a gradient correlation between a simple X-ray image and a pseudo X-ray image generated from a three-dimensional X-ray CT image.

Preferably, a registration parameter between the first image and the second image is input to the second converter, and the processor is configured to execute an optimization process of updating the registration parameter on the basis of the first similarity.

Preferably, the first image is a simple X-ray image, and the second image is a three-dimensional X-ray CT image.

Preferably, the second converter converts the three-dimensional X-ray CT image into an image obtained by correcting an attenuation value of the second image in a projection plane.

Preferably, the first converter converts the simple X-ray image on a two-dimensional feature image space with a model constructed using machine learning, and the second converter converts the three-dimensional X-ray CT image into the image obtained by correcting the attenuation value in the projection plane by masking a label of the region of interest on the three-dimensional X-ray CT image and projecting the masked three-dimensional X-ray CT image onto the two-dimensional feature image space.

According to another aspect of the present invention, there is provided a correct answer data generation device that generates correct answer data for learning interpretation of a simple X-ray image on the basis of the first similarity obtained by the above-described image processing device.

According to still another aspect of the present invention, there is provided a similar image search device that searches for a similar image on the basis of the first similarity obtained by the above-described image processing device.

According to yet another aspect of the present invention, there is provided an image processing method using an image processing device including a processor. The image processing method comprises causing the processor to execute: an image acquisition step of acquiring a first image in a first image space and a second image in a second image space different from the first image space; a first conversion step of converting the first image into an image in a third image space that is characterized by a region of interest, using a first converter; a second conversion step of converting the second image into an image in the third image space using a second converter; and a first similarity calculation step of calculating a first similarity between the first image and the second image in the third image space.

According to still yet another aspect of the present invention, there is provided a program causing an image processing device including a processor to execute an image processing method. The program causes the processor to execute: an image acquisition step of acquiring a first image in a first image space and a second image in a second image space different from the first image space; a first conversion step of converting the first image into an image in a third image space that is characterized by a region of interest, using a first converter; a second conversion step of converting the second image into an image in the third image space using a second converter; and a first similarity calculation step of calculating a first similarity between the first image and the second image in the third image space.

According to the present invention, the first image and the second image are converted on the third image space characterized by the region of interest, and the similarity between the converted first image and second image is calculated. Therefore, even in a case in which it is not easy to design the similarity of an input image in an image space, it is possible to easily calculate an interpretable similarity with high accuracy, without requiring correct answer data.

BRIEF DESCRIPTION OF THE DRAWINGS

FIG. 6 is a diagram illustrating calculation of a similarity in a first similarity calculation unit.

FIG. 14 is a diagram illustrating a second example.

FIG. 15 is a diagram illustrating a third example.

DESCRIPTION OF THE PREFERRED EMBODIMENTS

Hereinafter, preferred embodiments of an image processing device, a correct answer data generation device, a similar image search device, an image processing method, and a program according to embodiments of the present invention will be described with reference to the accompanying drawings.

First Embodiment

First, a first embodiment of the present invention will be described.

[Image Processing Device]

Figure 1:
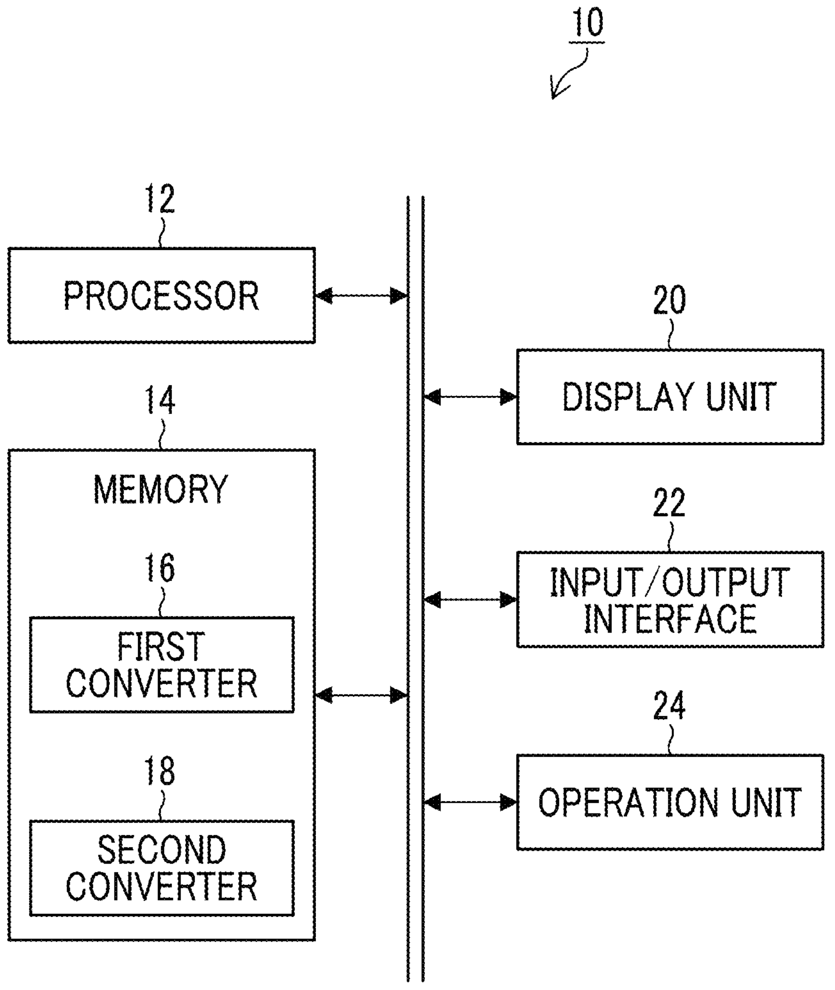
FIG. 1 is a block diagram illustrating an embodiment of a hardware configuration of an image processing device.

FIG. 1 is a block diagram illustrating an embodiment of a hardware configuration of an image processing device according to a first embodiment of the present invention.

An image processing device 10 illustrated in FIG. 1 can be configured by a personal computer, a workstation, or the like and comprises a processor 12, a memory 14, a display unit 20, an input/output interface 22, an operation unit 24, and the like.

The processor 12 is composed of a central processing unit (CPU) and the like and controls an overall operation of each unit of the image processing device 10. The processor 12 executes, for example, a first converter 16 (first converter program) and a second converter 18 (second converter program) stored in the memory 14. Further, the processor 12 functions as an image acquisition unit 30, a first conversion unit 32, a second conversion unit 34, a first similarity calculation unit 36, and an optimization unit 38 illustrated in FIG. 2. In addition, the processor 12 may be configured to include a graphics processing unit (GPU).

The memory 14 includes a flash memory, a read-only memory (ROM), a random access memory (RAM), a hard disk apparatus, and the like. The flash memory, the ROM, and the hard disk apparatus are non-volatile memories that store, for example, an operation system, the first converter 16, the second converter 18, and various programs causing the processor 12 to execute processes in each step of an image processing method according to the embodiment of the present invention. In addition, the hard disk apparatus can function as a large-capacity memory that stores simple X-ray images, three-dimensional X-ray computed tomography (CT) images, and anatomical labels corresponding to the three-dimensional X-ray CT images, which will be described below.

The RAM functions as a work area for processing by the processor 12 and temporarily stores the programs and the like stored in the non-volatile memory. Further, a portion (RAM) of the memory 14 may be provided in the processor 12.

The programs corresponding to the first converter 16 and the second converter 18 are stored in the memory 14. The processor 12 executes each of the program corresponding to the first converter 16 and the program corresponding to the second converter 18.

The first converter 16 receives a simple X-ray image 102 (first image) in a two-dimensional image space (first image space) as an input and converts the input simple X-ray image into an image in a two-dimensional feature image space (third image space) characterized by a region of interest. Specifically, the first converter 16 converts the simple X-ray image 102 (FIG. 3) into an image (separated image) in a feature image space characterized by an anatomical region of interest (for example, a bone, a lung, a heart, or an artery). The first converter 16 is a converter that is configured (constructed) by a conversion model (separation model) which is a trained model subjected to machine learning in advance. For example, the first converter 16 has been subjected to machine learning in advance to decompose the input simple X-ray image 102 into anatomical structures and to output the separated images.

The second converter 18 receives a three-dimensional X-ray CT image 106 (second image) in a three-dimensional image space (second image space) and an anatomical label 108 as an input and converts the three-dimensional X-ray CT image 106 into an image in the two-dimensional feature image space (third image space) characterized by the region of interest. Specifically, the second converter 18 masks a label corresponding to the region of interest on the three-dimensional X-ray CT image 106 on the basis of the input anatomical label 108 and projects the masked three-dimensional X-ray CT image 106 onto the two-dimensional feature image space. In this way, the second converter 18 converts the three-dimensional X-ray CT image 106 into the image (separated image) in the two-dimensional feature image space. Here, the separated image is an image having an attenuation value (attenuation) corrected in a projection plane by the second converter 18. In addition, the anatomical label 108 has three-dimensional label information of the anatomical structure of the three-dimensional X-ray CT image 106. Further, in this example, the anatomical label 108 of the three-dimensional X-ray CT image 106 is input. However, the present invention is not limited thereto. Structural label information of the three-dimensional X-ray CT image 106 may be input.

Furthermore, the first converter 16 and the second converter 18 perform conversion into an image (separated image) in the feature image space characterized by the region of interest. The region of interest is received from the operation unit 24 and is input to the processor 12 (region-of-interest receiving process). Moreover, the reception of the region of interest is not limited to the reception from the operation unit 24, and a preset region of interest may be used.

The display unit 20 is configured by a display such as a liquid crystal monitor. Various types of necessary information are displayed on the display unit 20. For example, the display unit 20 displays the similarity or final registration parameters calculated by the image processing device 10. In addition, the display unit 20 can be used as a portion of a user interface in a case in which various instructions of the user are received.

The input/output interface 22 includes, for example, a connection unit that can be connected to an external apparatus and a communication unit that can be connected to a network. For example, a universal serial bus (USB) or a high-definition multimedia interface (HDMI) (HDMI is a registered trademark) can be applied as the connection unit that can be connected to the external apparatus. The processor 12 can acquire the simple X-ray image 102, the three-dimensional X-ray CT image 106, the anatomical label 108, and various programs stored in the memory 14 through the input/output interface 22. In addition, an external display device connected to the input/output interface 22 can be used instead of the display unit 20.

The operation unit 24 includes a keyboard, a pointing device, such as a mouse and functions as a user interface that receives various designations.

Figure 2:
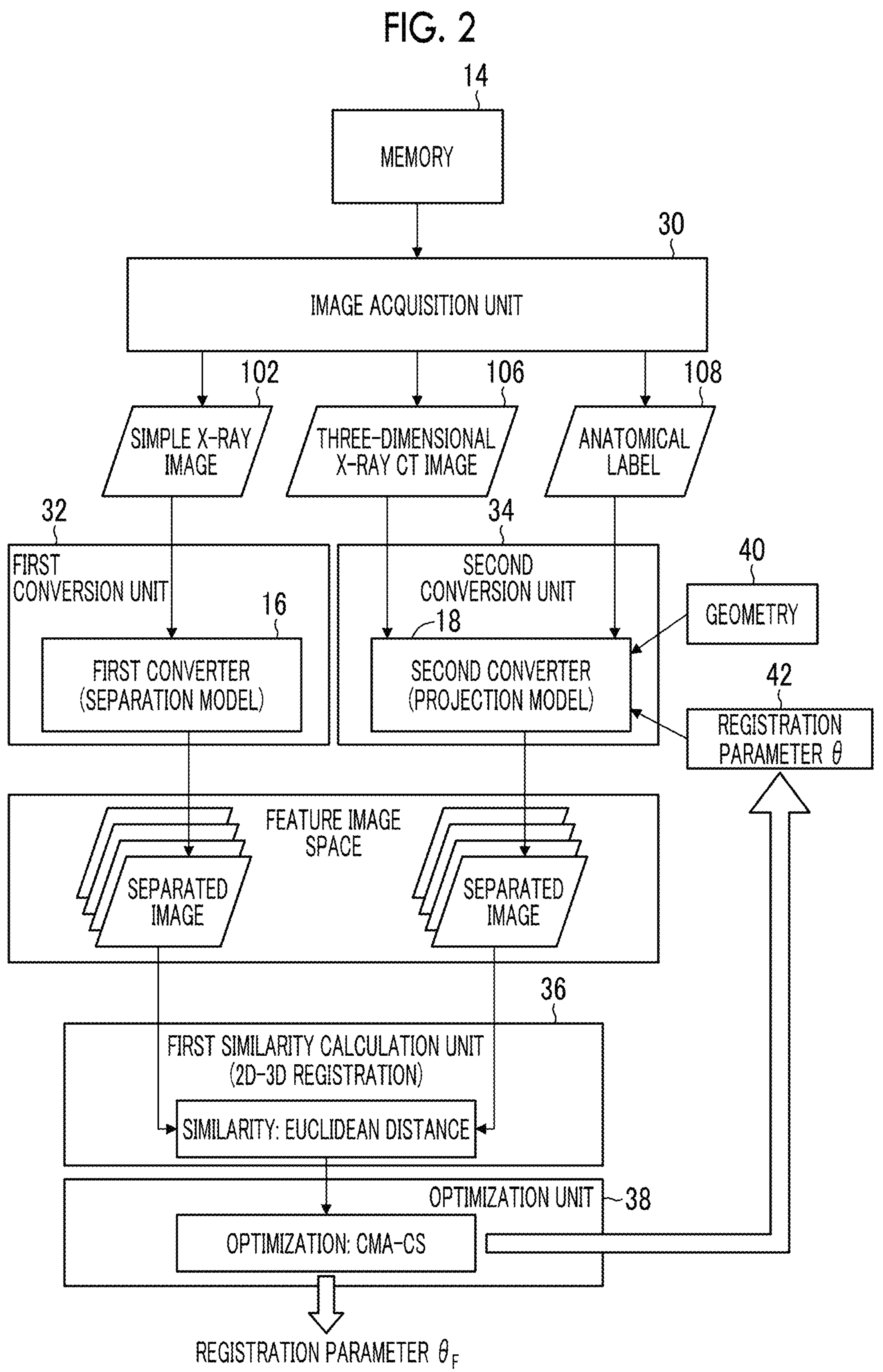
FIG. 2 is a functional block diagram illustrating the image processing device.

FIG. 2 is a functional block diagram illustrating the image processing device 10 according to the first embodiment of the present invention. Further, in the following description, an example will be described in which a similarity (first similarity) between the simple X-ray image 102 and the three-dimensional X-ray CT image 106 of the chest of the same patient (patient A) is calculated and the registration parameters of the simple X-ray image 102 and the three-dimensional X-ray CT image 106 based on the similarity are output. In addition, in this example, an example has been described in which the simple X-ray image 102 is used as an example of the first image and the three-dimensional X-ray CT image 106 is used as an example of the second image. However, the present invention is not limited thereto. Preferably, a two-dimensional image is used as the first image, and a three-dimensional image is used as the second image.

The image processing device 10 is configured by the memory 14 and the processor 12 having the hardware configuration illustrated in FIG. 1. As described above, the processor 12 functions as the image acquisition unit 30, the first conversion unit 32, the second conversion unit 34, the first similarity calculation unit 36, and the optimization unit 38.

The image acquisition unit 30 performs an image acquisition process to acquire the simple X-ray image 102, the three-dimensional X-ray CT image 106, and the anatomical label 108 corresponding to the three-dimensional X-ray CT image 106 stored in the memory 14. The simple X-ray image 102, the three-dimensional X-ray CT image 106, and the anatomical label 108 are data for the same patient A. The simple X-ray image 102 is an X-ray image obtained by irradiating the patient A with X-rays in one direction. The three-dimensional X-ray CT image 106 is an image generated by irradiating a body of the patient A with X-rays while rotating around the body of the patient A, collecting three-dimensional information of the inside of the body, and performing computer processing. In addition, the anatomical label 108 is label information indicating an anatomical structure, such as an organ or a bone of the patient A, obtained on the basis of the three-dimensional X-ray CT image 106. The image acquisition unit 30 acquires the simple X-ray image 102 as a two-dimensional input and acquires the three-dimensional X-ray CT image 106 and the anatomical label 108 as a three-dimensional input.

The first conversion unit 32 performs a first conversion process using the first converter 16. The first conversion unit 32 converts the simple X-ray image 102 into a separated image in the feature image space (third image space) characterized by the region of interest, using the first converter 16. In this example, anatomical regions of interest are adopted as the regions of interest, and four regions of a bone, a lung, a heart, and an artery in the chest of the human body are adopted.

Figure 3:
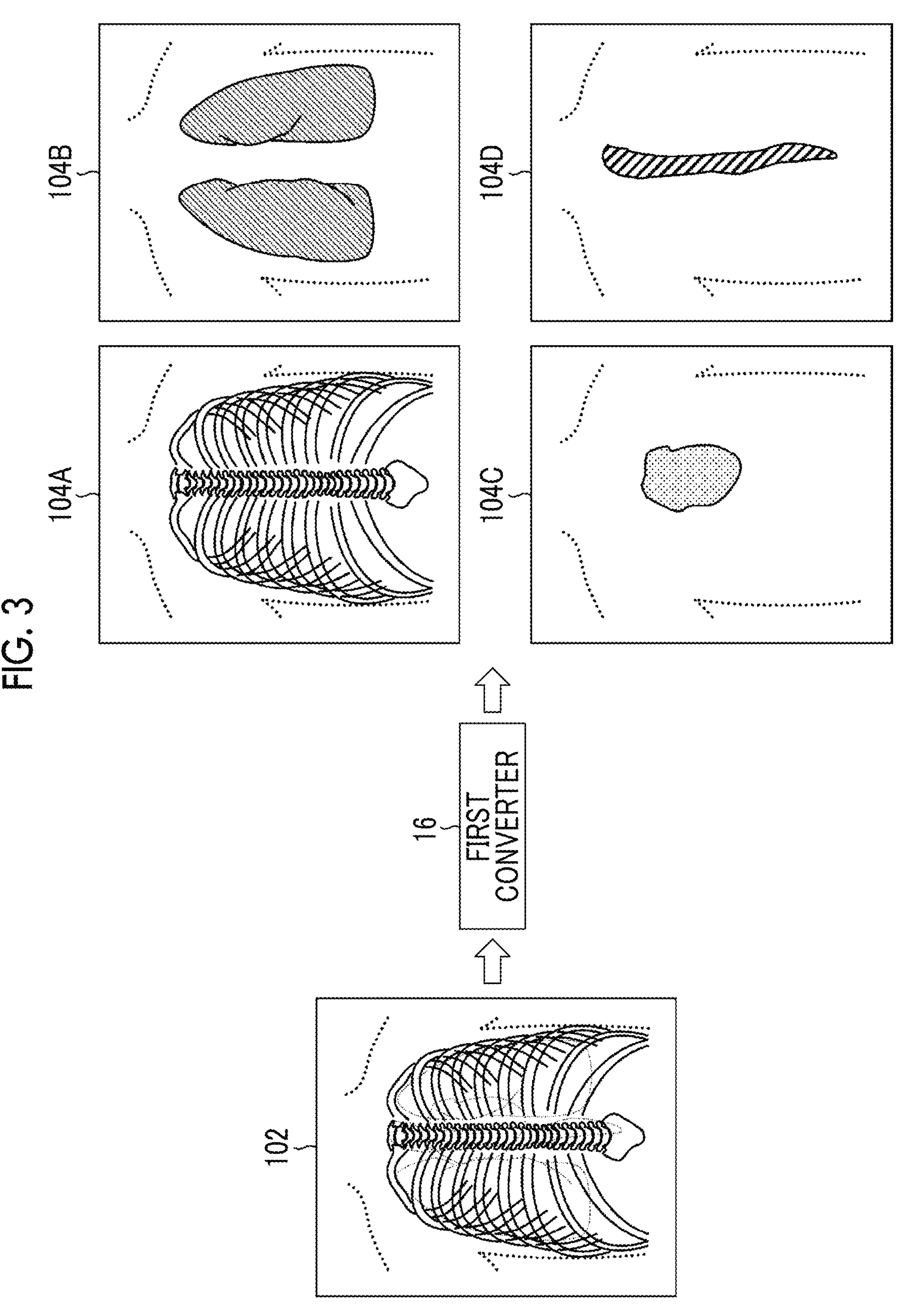
FIG. 3 is a diagram illustrating a process of a first conversion unit.

FIG. 3 is a diagram illustrating the process of the first conversion unit 32.

The first conversion unit 32 has the first converter 16, and the simple X-ray image 102 obtained by imaging the chest of the human body is input to the first converter 16. Then, the first converter 16 converts the simple X-ray image 102 into a separated image in the feature image space characterized by the region of interest. Specifically, the first converter 16 converts the simple X-ray image 102 into a feature image space of the bone, a feature image space of the lung, a feature image space of the heart, a feature image space of an aorta as the feature image spaces characterized by the regions of interest. FIG. 3 illustrates a separated image 104A converted into the feature image space of the bone, a separated image 104B converted into the feature image space of the lung, a separated image 104C converted into the feature image space of the heart, and a separated image 104D converted into the feature image space of the aorta. Further, in this example, the simple X-ray image 102 is converted into images in a plurality of feature image spaces. However, the present invention is not limited thereto. For example, the simple X-ray image 102 may be converted into an image in a single feature image space.

The second conversion unit 34 (FIG. 2) performs a second conversion process using the second converter 18. The second conversion unit 34 converts the three-dimensional X-ray CT image 106 into a separated image in the feature image space (third image space) characterized by the region of interest, using the second converter 18. Here, in this example, as described above, the anatomical region of interest is adopted as the region of interest, and four regions of the bone, the lung, the heart, and the artery in the chest of the human body are adopted.

Figure 4:
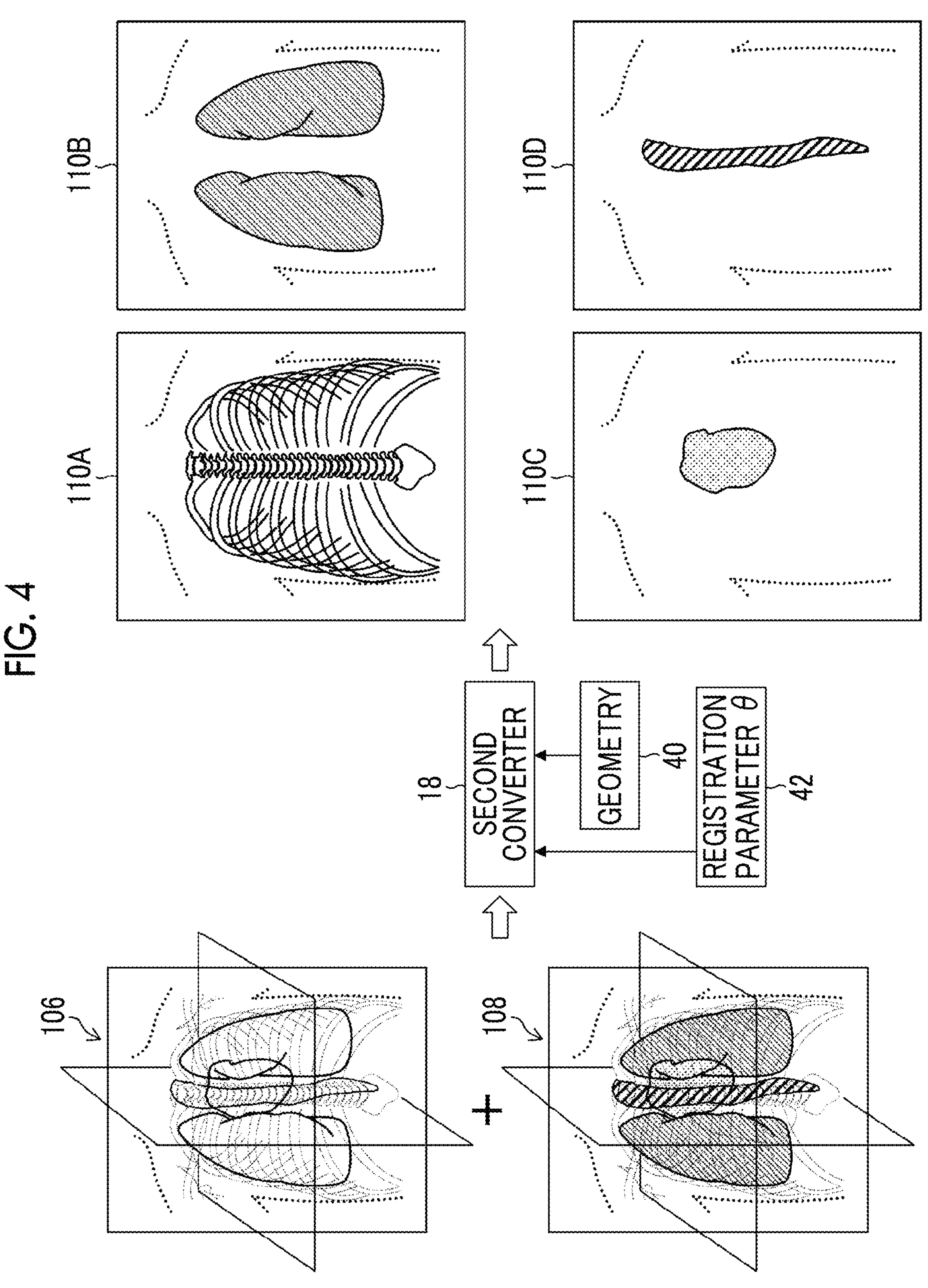
FIG. 4 is a diagram illustrating a process of a second conversion unit.

FIG. 4 is a diagram illustrating the process of the second conversion unit 34.

The second conversion unit 34 has the second converter 18, and the three-dimensional X-ray CT image 106 obtained by imaging the chest of the human body and the anatomical label 108 are input to the second converter 18. Further, a geometry 40 and a registration parameter θ (indicated by reference numeral 42) are input to the second converter 18. Here, the geometry 40 is information related to an X-ray examination apparatus including imaging conditions for capturing the three-dimensional X-ray CT image 106. The geometry 40 includes, for example, a source-to-object distance (SOD), a source-to-detector distance (SDD), and general X-ray imaging conditions. In addition, the registration parameter θ is a deformation parameter for the three-dimensional X-ray CT image 106 as described below. Further, θ (initial) is set as an initial value of the registration parameter θ, and the registration parameter θ is updated by the optimization unit 38 which will be described below. A registration parameter $\theta_F$ that maximizes the similarity is calculated.

Figure 5:
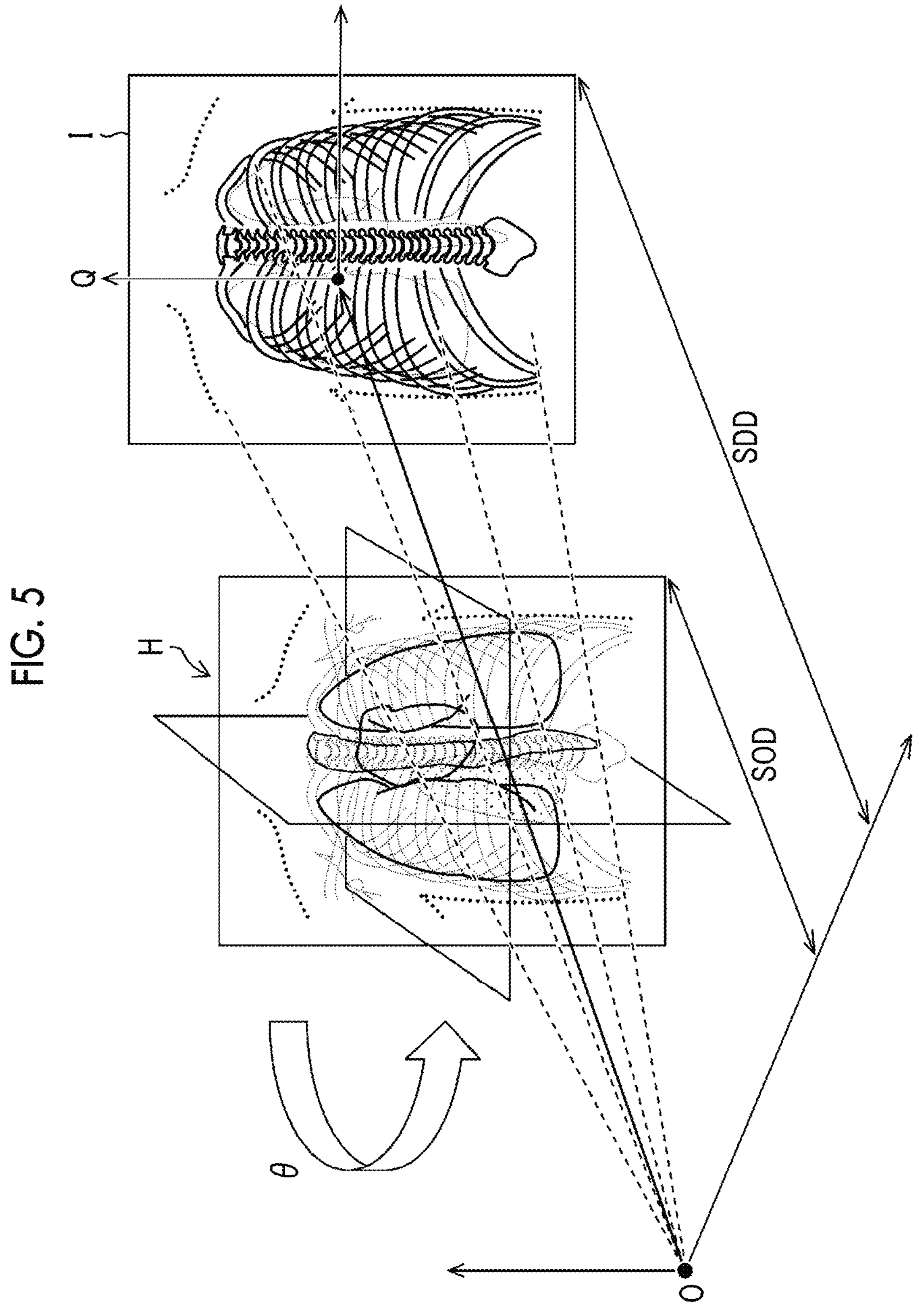
FIG. 5 is a diagram illustrating a registration parameter θ.

FIG. 5 is a diagram illustrating the registration parameter θ.

FIG. 5 illustrates a virtual X-ray source O and a virtual detector Q. Assuming that X-rays are emitted from the virtual X-ray source O, in a case in which a virtual three-dimensional human body corresponding to a three-dimensional X-ray CT image H is disposed at the SOD, the virtual detector Q detects a projected two-dimensional simple X-ray image I. The simple X-ray image I can be changed by changing the registration parameter θ. In addition, the registration parameter θ is a parameter for changing the direction and inclination of the three-dimensional X-ray CT image 106 and is also a parameter for deforming the organ in the three-dimensional X-ray CT image 106 in the second converter 18. Further, in this example, the description has been made on the premise of rigid deformation. However, the three-dimensional X-ray CT image H may be deformed and registered using a well-known non-rigid deformation method.

Returning to FIG. 4, as described above, the three-dimensional X-ray CT image 106, the anatomical label 108, the geometry 40, and the registration parameter θ (reference numeral 42) are input to the second converter 18. Then, the second converter 18 converts the three-dimensional X-ray CT image 106 into a separated image 110A projected to the feature image space of the bone, a separated image 110B projected to the feature image space of the lung, a separated image 110C projected to the feature image space of the heart, and a separated image 110D projected to the feature image space of the aorta.

The first similarity calculation unit 36 (FIG. 2) performs a first similarity calculation process to calculate the similarities between the separated images in each of the feature image spaces characterized by the regions of interest converted by the first conversion process and the second conversion process. The first similarity calculation unit 36 can calculate the similarities between the separated images using various methods. For example, the first similarity calculation unit 36 calculates the similarities using a Euclidean distance. For example, in a case in which the separated image 104A and the separated image 110A are composed of n×m pixels, the first similarity calculation unit 36 can calculate the distance between the separated image 104A and the separated image 110A as an n×m-dimensional vector using the Euclidean distance to obtain the similarity. Similarly, the first similarity calculation unit 36 can calculate the similarity between the separated image 104B and the separated image 110B, the similarity between the separated image 104C and the separated image 110C, and the similarity between the separated image 104D and the separated image 110D. Then, the first similarity calculation unit 36 integrates the similarities calculated in each feature image space.

FIG. 6 is a diagram illustrating the calculation of the similarity in the first similarity calculation unit 36.

The first similarity calculation unit 36 calculates the similarities in each feature image space and integrates the calculated similarities to calculate the similarity (total) between the simple X-ray image 102 and the three-dimensional X-ray CT image 106. Specifically, the first similarity calculation unit 36 integrates the similarity (bone) calculated between the separated images (the separated image 104A and the separated image 110A) in the feature image space of the bone, the similarity (lung) calculated between the separated images (the separated image 104B and the separated image 110B) in the feature image space of the lung, the similarity (heart) calculated between the separated images (the separated image 104C and the separated image 110C) in the feature image space of the heart, and the similarity (artery) calculated from the separated images (the separated image 104D and the separated image 110D) of the feature image space of the artery to calculate the similarity (total). Here, the first similarity calculation unit 36 integrates the similarities to calculate the similarity (total), using various methods. For example, the first similarity calculation unit 36 adds, multiplies, or averages the similarities to calculate the similarity (total) which is one scalar. As described above, in this embodiment, even in a case in which it is not easy to design the similarity between the input images in the image space, it is possible to calculate the similarity in the feature image space characterized by the region of interest with high accuracy. In addition, in this embodiment, since the similarity is calculated in each feature image space, it is possible to understand the feature image space having a high or low similarity and to calculate an interpretable similarity. Further, in this embodiment, in a case in which the similarity is calculated, it is possible to calculate the similarity with high accuracy without requiring correct answer data.

The optimization unit 38 (FIG. 2) performs an optimization process. Specifically, the optimization unit 38 optimizes the registration parameter θ on the basis of the similarity (total) calculated by the first similarity calculation unit 36. For example, the optimization unit 38 updates the registration parameter θ using an optimization algorithm (covariance matrix adaptation evolution strategy (CMA-ES)) and calculates a registration parameter $\theta_F$ that maximizes the similarity. As described above, the optimization unit 38 can optimize the registration parameter θ to acquire the registration parameter $\theta_F$ that maximizes the similarity.

[Image Processing Method]

Next, an image processing method using the image processing device 10 will be described.

Figure 7:
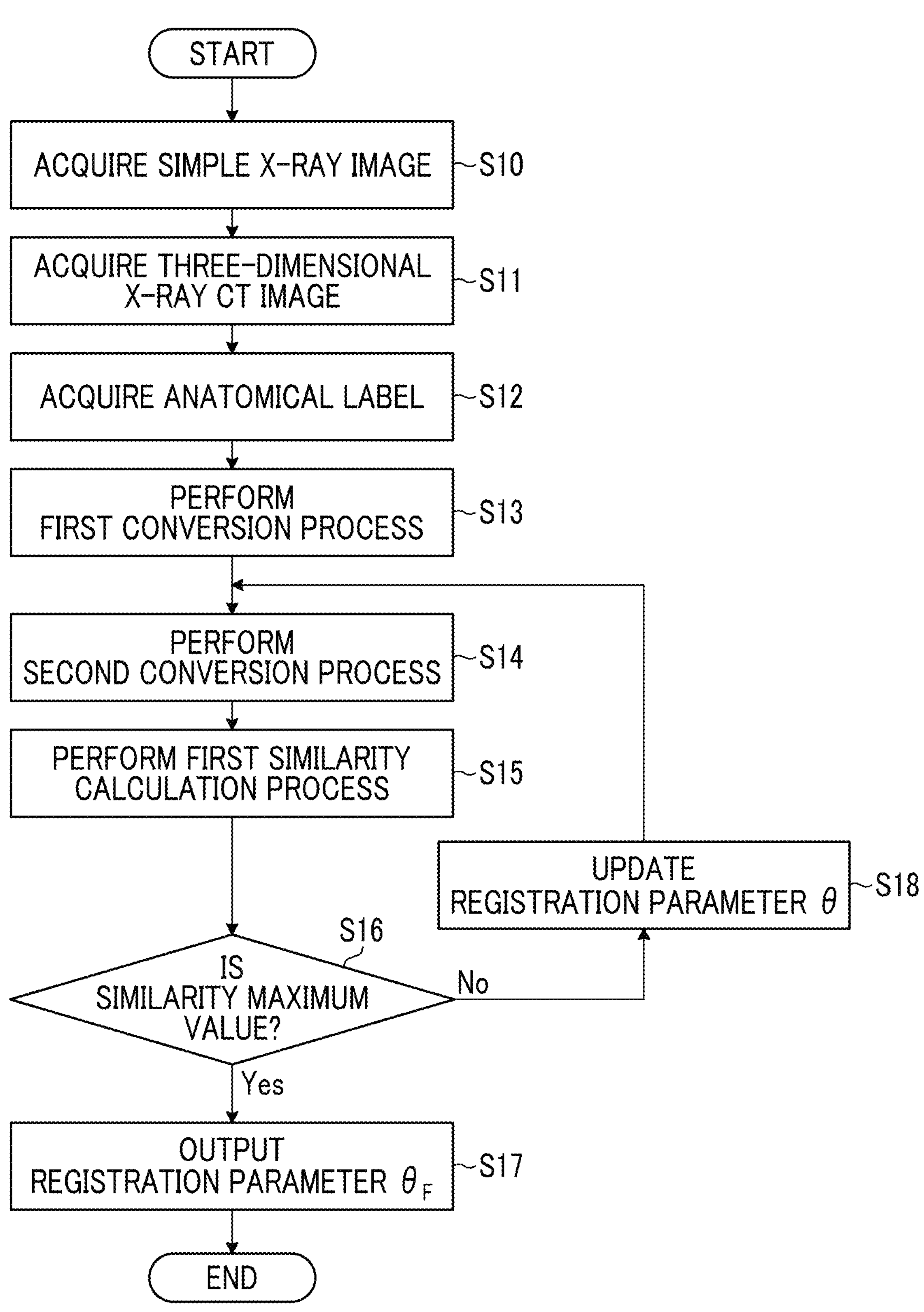
FIG. 7 is a flowchart illustrating an image processing method using the image processing device.

FIG. 7 is a flowchart illustrating the image processing method using the image processing device 10. In addition, the processor 12 of the image processing device 10 executes a dedicated program to perform each step of the image processing method.

First, the image acquisition unit 30 acquires, for example, the simple X-ray image 102 stored in the memory 14 (Step S10: image acquisition step). In addition, the image acquisition unit 30 acquires, for example, the three-dimensional X-ray CT image 106 stored in the memory 14 (Step S11: image acquisition step). Further, the image acquisition unit 30 acquires, for example, the anatomical label 108 corresponding to the three-dimensional X-ray CT image 106 stored in the memory 14 (Step S12). Then, the first conversion unit 32 performs the first conversion process (Step S13: first conversion step). Specifically, the first conversion unit 32 converts the simple X-ray image 102 into the separated images 104A to 104D. Then, the second conversion unit 34 performs the second conversion process (Step S14: second conversion step). Specifically, the second conversion unit 34 converts the three-dimensional X-ray CT image 106 into the separated images 110A to 110D. Then, the first similarity calculation unit 36 calculates the similarity between the simple X-ray image 102 and the three-dimensional X-ray CT image 106 (Step S15: first similarity calculation step). Then, the optimization unit 38 determines whether or not the calculated similarity has a maximum value (Step S16). In a case in which the calculated similarity does not have the maximum value, the optimization unit 38 updates the registration parameter θ (Step S18). Then, the second conversion process (Step S14) is performed again on the basis of the updated registration parameter θ. In the second conversion process, the conversion into the separated images 110A to 110D is performed on the basis of the updated registration parameter θ. On the other hand, in a case in which the calculated similarity has the maximum value, the registration parameter $\theta_F$ at which the maximum similarity has been calculated is output (Step S17).

As described above, according to this embodiment, the simple X-ray image 102 and the three-dimensional X-ray CT image 106 are converted into the feature image spaces characterized by the regions of interest, and the similarities between the separated images 104A to 104D and the separated images 110A to 110D after the conversion are calculated. Therefore, even in a case in which it is not easy to design the similarity between the input images in the image space, it is possible to easily calculate an interpretable similarity with high accuracy without requiring correct answer data.

Modification Example 1 of First Embodiment

Next, Modification Example 1 of this embodiment will be described. In this example, in the first conversion process and the second conversion process, conversion into separated images is performed using a plurality of converters.

Figure 8:
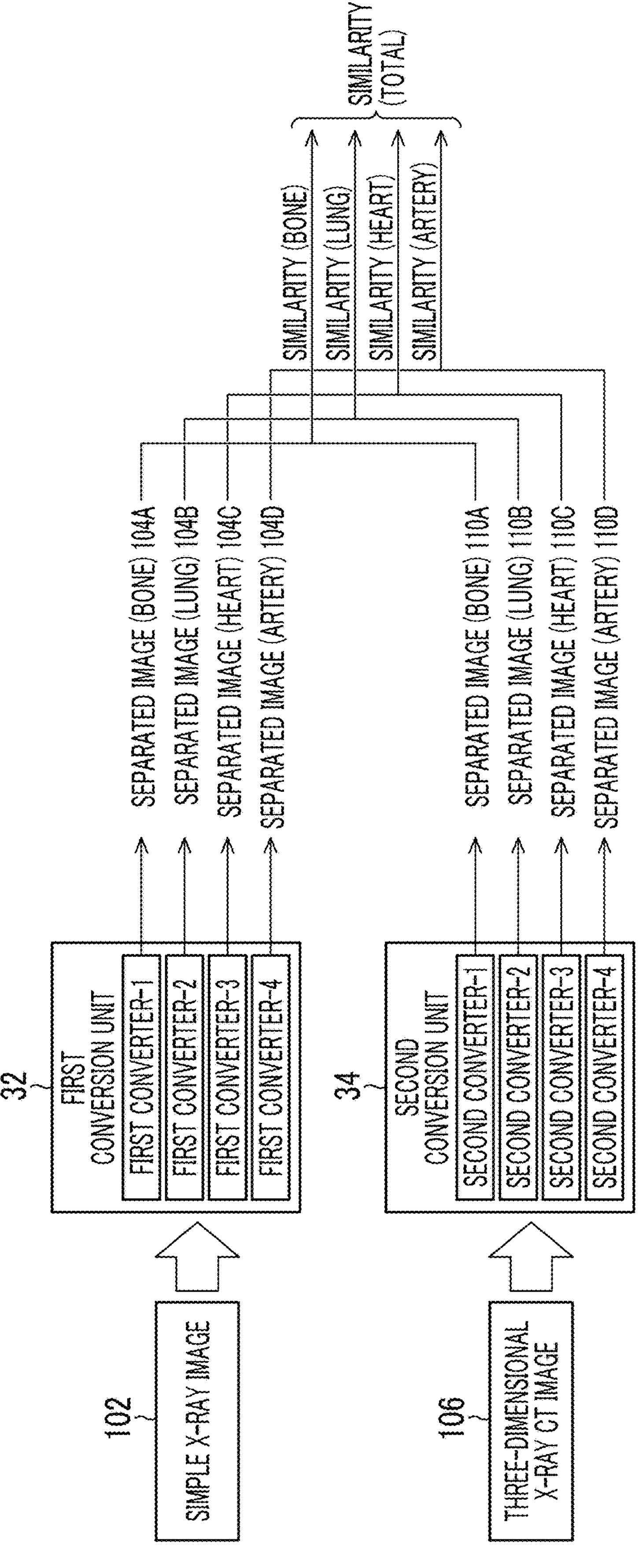
FIG. 8 is a diagram illustrating a first conversion unit and a second conversion unit according to Modification Example 1.

FIG. 8 is a diagram illustrating a first conversion unit 32 and a second conversion unit 34 according to Modification Example 1. In addition, the portions already described in FIG. 6 are denoted by the same reference numerals, and the description thereof will not be repeated.

The first conversion unit 32 comprises a first converter-1, a first converter-2, a first converter-3, and a first converter-4. The first conversion unit 32 converts the simple X-ray image 102 into the separated image 104A, the separated image 104B, the separated image 104C, and the separated image 104D using the first converter-1, the first converter-2, the first converter-3, and the first converter-4, respectively.

The second conversion unit 34 comprises a second converter-1, a second converter-2, a second converter-3, and a second converter-4. The second conversion unit 34 converts the three-dimensional X-ray CT image 106 into the separated image 110A, the separated image 110B, the separated image 110C, and the separated image 110D using the second converter-1, the second converter-2, the second converter-3, and the second converter-4, respectively. As described above, the first conversion unit 32 and the second conversion unit 34 according to this example comprise a plurality of converters and perform conversion into the separated images in the feature image spaces corresponding to each converter.

Then, the first similarity calculation unit 36 according to this example calculates similarities (a similarity (bone), a similarity (lung), a similarity (heart), and a similarity (artery)) for the images in each feature image space and integrates the similarities in each feature image space.

As described above, in this example, the first conversion unit 32 and the second conversion unit 34 comprise a plurality of converters corresponding to the feature image spaces to be converted. As described above, since a plurality of converters corresponding to the feature image spaces are provided, it is possible to perform conversion more suitable for the feature image spaces.

Modification Example 2 of First Embodiment

Next, Modification Example 2 of this embodiment will be described. In this example, the first converter 16 outputs a first reliability indicating the reliability of the separated image after conversion, and the second converter 18 outputs a second reliability indicating the reliability of the separated image after conversion. The first reliability and the second reliability may be output for each separated image or may be output for each pixel of the separated image.

Here, the reliability is a value indicating the certainty of the separated image after conversion. The first converter is configured by a trained model (conversion model (separation model)) as described above, and the second converter is configured by a trained model (conversion model (projection model)) as described above. Therefore, in a case in which data that is different or heterogeneous from the training data subjected to machine learning is input to the first converter, the reliability of the separated image converted by the first converter 16 is reduced. On the other hand, in a case in which the same data as the training data subjected to machine learning is input to the first converter 16, the reliability of the separated image converted by the first converter 16 is increased. Similarly, in a case in which data that is different or heterogeneous from the training data subjected to machine learning is input to the second converter 18, the reliability of the separated image to be converted by the second converter is reduced. On the other hand, in a case in which the same data as the training data subjected to machine learning is input to the second converter, the reliability of the separated image converted by the second converter 18 is increased.

Figure 9:
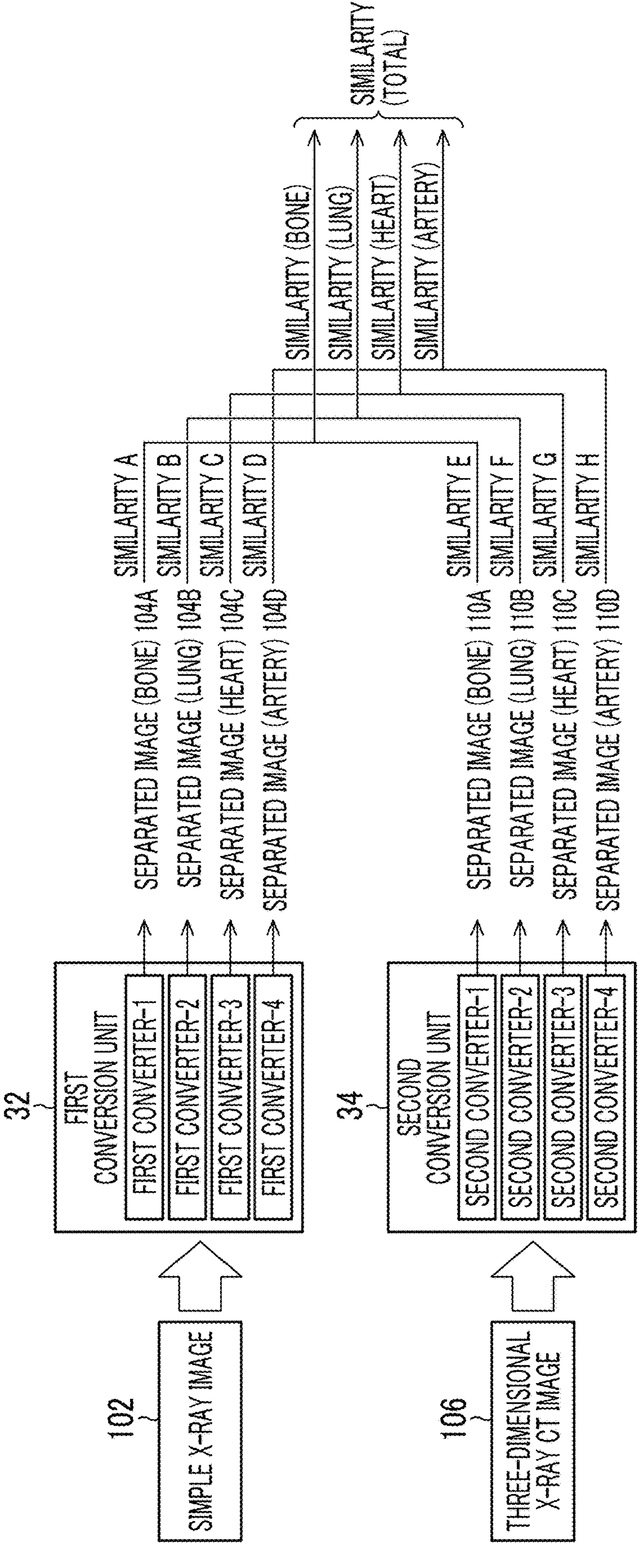
FIG. 9 is a diagram illustrating a reliability.

FIG. 9 is a diagram illustrating the reliability. In addition, the portions already described in FIGS. 6 and 8 are denoted by the same reference numerals, and the description thereof will not be repeated.

The first converter-1 outputs a reliability A for the separated image 104A, the first converter-2 outputs a reliability B for the separated image 104B, the first converter-3 outputs a reliability C for the separated image 104C, and the first converter-4 outputs a reliability D for the separated image 104D. In addition, the second converter-1 outputs a reliability E for the separated image 110A, the second converter-2 outputs a reliability F for the separated image 110B, the second converter-3 outputs a reliability G for the separated image 110C, and the second converter-4 outputs a reliability H for the separated image 110D.

Then, the first similarity calculation unit 36 performs weighting on the basis of the reliability A and the reliability E in a case in which the similarity (bone) between the separated image 104A and the separated image 110A is calculated. Further, the first similarity calculation unit 36 performs weighting on the basis of the reliability B and the reliability F in a case in which the similarity (lung) between the separated image 104B and the separated image 110B is calculated. Furthermore, the first similarity calculation unit 36 performs weighting on the basis of the reliability C and the reliability G in a case in which the similarity (heart) between the separated image 104C and the separated image 110C is calculated. Moreover, the first similarity calculation unit 36 performs weighting on the basis of the reliability D and the reliability H in a case in which the similarity (artery) between the separated image 104D and the separated image 110D is calculated. Then, the first similarity calculation unit 36 integrates the similarity (bone), the similarity (lung), the similarity (heart), and the similarity (artery) to calculate the similarity (total). The first similarity calculation unit 36 calculates the similarity (total) weighted on the basis of the reliabilities A to H. Specifically, the similarity (bone), the similarity (lung), the similarity (heart), and the similarity (artery) are weighted on the basis of the reliabilities A to H, respectively, and the similarity (total) obtained by integrating the similarity (bone), the similarity (lung), the similarity (heart), and the similarity (artery) is also weighted on the basis of the reliabilities A to H. As described above, since the similarity (total) is weighted on the basis of the reliabilities, it is possible to output the registration parameter $\theta_F$ with higher accuracy. Further, in the above-mentioned example, the aspect has been described in which all of the first converter-1 to the first converter-4 and the second converter-1 to the second converter-4 output the reliability. However, the present invention is not limited thereto. For example, the reliability may be output only from the first converters (the first converter-1 to the first converter-4), and the similarity (total) having a weight may be calculated on the basis of the reliability. Further, the reliability may be output only from the second converters (second converter-1 to second converter-4), and the similarity (total) having a weight may be calculated on the basis of the reliability. In addition, selection may be performed on the basis of the reliabilities A to H to calculate each similarity. Specifically, for example, the separated image having a relatively low reliability may be excluded, and the similarity may be calculated.

Modification Example 3 of First Embodiment

Next, Modification Example 3 of this embodiment will be described. In this example, a second similarity calculation unit 120 is further provided to calculate a pre-conversion similarity (second similarity) which is a similarity between the simple X-ray image 102 and the three-dimensional X-ray CT image 106 before conversion by the first conversion unit 32 and the second conversion unit 34.

Figure 10:
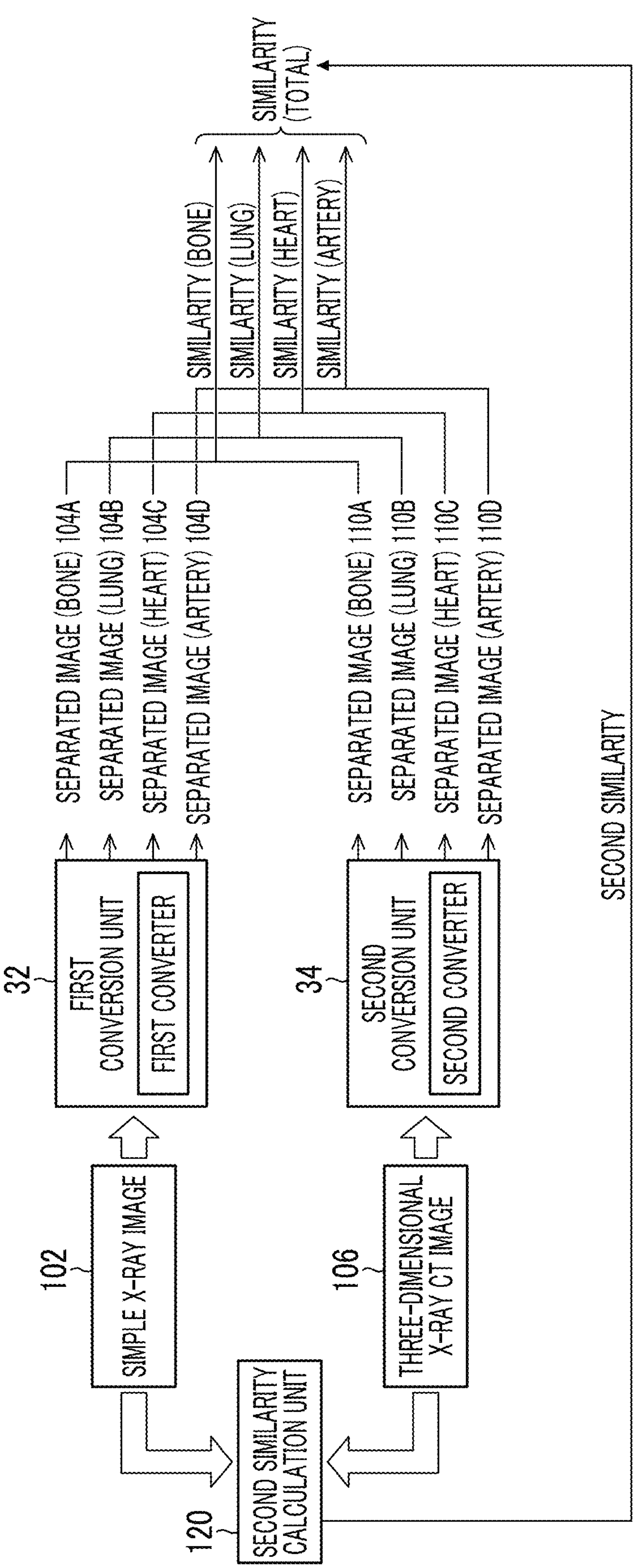
FIG. 10 is a diagram illustrating the calculation of the similarity in the first similarity calculation unit.

FIG. 10 is a diagram illustrating the calculation of the similarity in the second similarity calculation unit 120 according to this example. In addition, the portions already described in FIG. 6 are denoted by the same reference numerals, and the description thereof will not be repeated.

The second similarity calculation unit 120 performs a second similarity calculation process by the execution of the program stored in the memory by the processor 12. The simple X-ray image 102 and the three-dimensional X-ray CT image 106 are input to the second similarity calculation unit 120. The second similarity calculation unit 120 calculates the pre-conversion similarity on the basis of the simple X-ray image 102 and the three-dimensional X-ray CT image 106. Here, the second similarity calculation unit 120 calculates the pre-conversion similarity before the simple X-ray image 102 and the three-dimensional X-ray CT image 106 are converted by the first conversion unit 32 and the second conversion unit 34, respectively. The second similarity calculation unit 120 can calculate the pre-conversion similarity between the simple X-ray image 102 and the three-dimensional X-ray CT image 106 using a known method. For example, the second similarity calculation unit 120 superimposes bone portions in the simple X-ray image 102 and the three-dimensional X-ray CT image 106 to calculate the pre-conversion similarity. In addition, for example, the second similarity calculation unit 120 calculates, as the pre-conversion similarity, an amount of mutual information between the simple X-ray image 102 and a pseudo X-ray image generated from the three-dimensional X-ray CT image 106. Further, for example, the second similarity calculation unit 120 calculates, as the pre-conversion similarity, a gradient correlation between the simple X-ray image 102 and the pseudo X-ray image generated from the three-dimensional X-ray CT image 106. Here, the pseudo X-ray image is generated by the second similarity calculation unit 120. The second similarity calculation unit 120 generates a pseudo X-ray image that imitates the two-dimensional simple X-ray image from the three-dimensional X-ray CT image 106 using a known method.

The first similarity calculation unit 36 calculates a similarity obtained by weighting the calculated similarity (total) on the basis of the pre-conversion similarity. Then, the optimization unit 38 optimizes the registration parameter θ on the basis of the weighted similarity.

As described above, the similarity weighted on the basis of the pre-conversion similarity is output, which makes it possible to efficiently optimize the registration parameter θ.

Application Example of First Embodiment

Next, an application example using the similarity and the registration parameter $\theta_F$ calculated in the above-described embodiment will be described.

As described above, according to this embodiment, it is possible to acquire the similarity and the registration parameter $\theta_F$ with high accuracy. The similarity and the registration parameter $\theta_F$ can be used for various purposes.

For example, the registration parameter $\theta_F$ calculated by the image processing device 10 can be used for a correct answer data generation device that generates correct answer data for performing machine learning on a detector which interprets the simple X-ray image.

Figure 11:
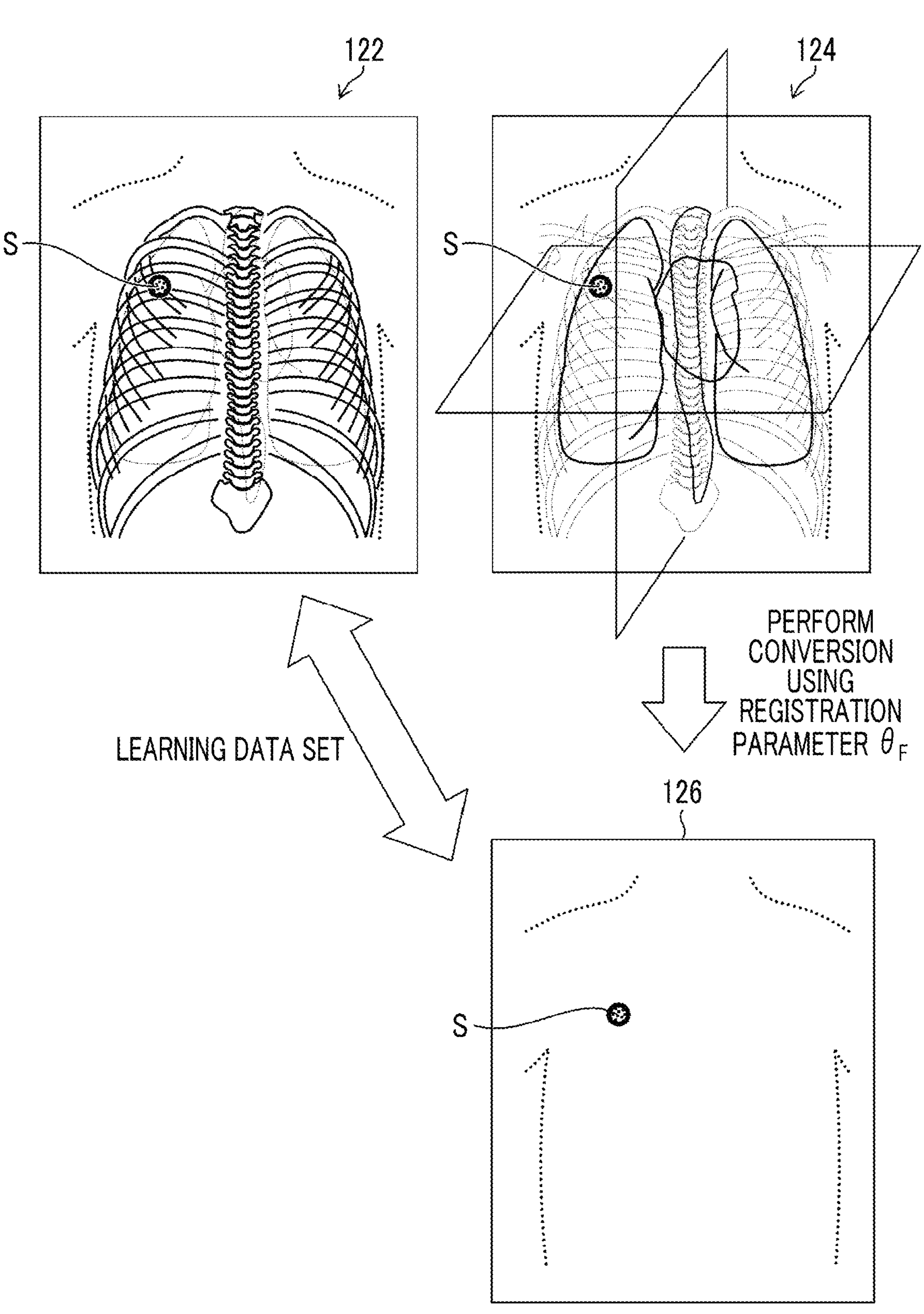
FIG. 11 is a diagram illustrating generation of a learning data set including correct answer data.

FIG. 11 is a diagram illustrating generation of a learning data set including correct answer data.

FIG. 11 illustrates a simple X-ray image 122 and a three-dimensional X-ray CT image 124 of a patient B. The patient B has a lesion portion S in the lung. Here, the maximum similarity between the simple X-ray image 122 and the three-dimensional X-ray CT image 124 is calculated by the image processing device 10, and the registration parameter $\theta_F$ is calculated. Therefore, correct answer data 126 having the lesion portion S can be generated by inputting the three-dimensional X-ray CT image 124 and the registration parameter $\theta_F$ to the correct answer data generation device comprising a converter (projection model). The correct answer data 126 is data corresponding to the two-dimensional simple X-ray image 122. The position of the lesion portion S is accurately projected onto the correct answer data 126. Therefore, machine learning can be performed by performing learning such that an error between the correct answer data 126 and an interpretation result output from the detector, which receives the input of the simple X-ray image 122 and interprets the simple X-ray image 122, is reduced. As described above, the use of the registration parameter $\theta_F$ makes it possible to efficiently generate correct answer data for performing machine learning on the interpretation of the simple X-ray image.

Another example is a similar image search device that searches for a similar image on the basis of the similarity calculated by the image processing device 10. Specifically, for example, in a case in which a three-dimensional X-ray CT image similar to a simple X-ray image is searched for, the similar image is searched for on the basis of the similarity calculated by the image processing device 10. For example, a three-dimensional X-ray CT image having the maximum similarity with the input simple X-ray image can be extracted as the similar image.

Second Embodiment

Next, a second embodiment will be described. In the first embodiment, an example has been described in which the first converter 16 converts the simple X-ray image 102 into the separated images and the second converter 18 converts the three-dimensional X-ray CT image 106 into the separated images. In the second embodiment, the first converter 16 converts the simple X-ray image 102 into a shape feature and a texture feature, and the second converter 18 converts the three-dimensional X-ray CT image 106 into a shape feature and a texture feature.

The existing similarities are broadly divided into measures based on the shape feature or the texture feature. A technique related to registration using the similarity based on the shape feature is described in, for example, Toth, Daniel, et al. "3D/2D model-to-image registration by imitation learning for cardiac procedures.", IJCARS, 2018. and Ruijters, Daniel, Bart M. ter Haar Romeny, and Paul Suetens. "Vesselness-based 2D-3D registration of the coronary arteries." International journal of computer assisted radiology and surgery 4.4 (2009): 391-397. In addition, a technique related to registration using the similarity based on the texture feature is disclosed in, for example, Van der Bom, I. M. J., et al. "Evaluation of optimization methods for intensity-based 2D-3D registration in x-ray guided interventions.", Medical Imaging, 2011. and Hiasa, Yuta, et al. "Recovery of 3D rib motion from dynamic chest radiography and CT data using local contrast normalization and articular motion model." Medical Image Analysis, 2019.

In the registration using the shape features, since global anatomical registration is performed, accuracy is low, but robustness against disturbance is relatively high. On the other hand, in the registration using the texture feature, since local registration is performed, accuracy is high, but robustness is relatively low. As described above, there is a trade-off relationship between the registration using the shape feature and the registration using the texture feature.

Therefore, in this embodiment, the above-mentioned trade-off between the shape feature and the texture feature can be automatically adjusted to calculate the similarity with high accuracy and high robustness. In addition, in this embodiment, as in the first embodiment, since the similarity is not automatically designed by metric learning, it is possible to provide the similarity that can be interpreted by humans.

First, the shape feature and the texture feature will be described.

Figure 12:
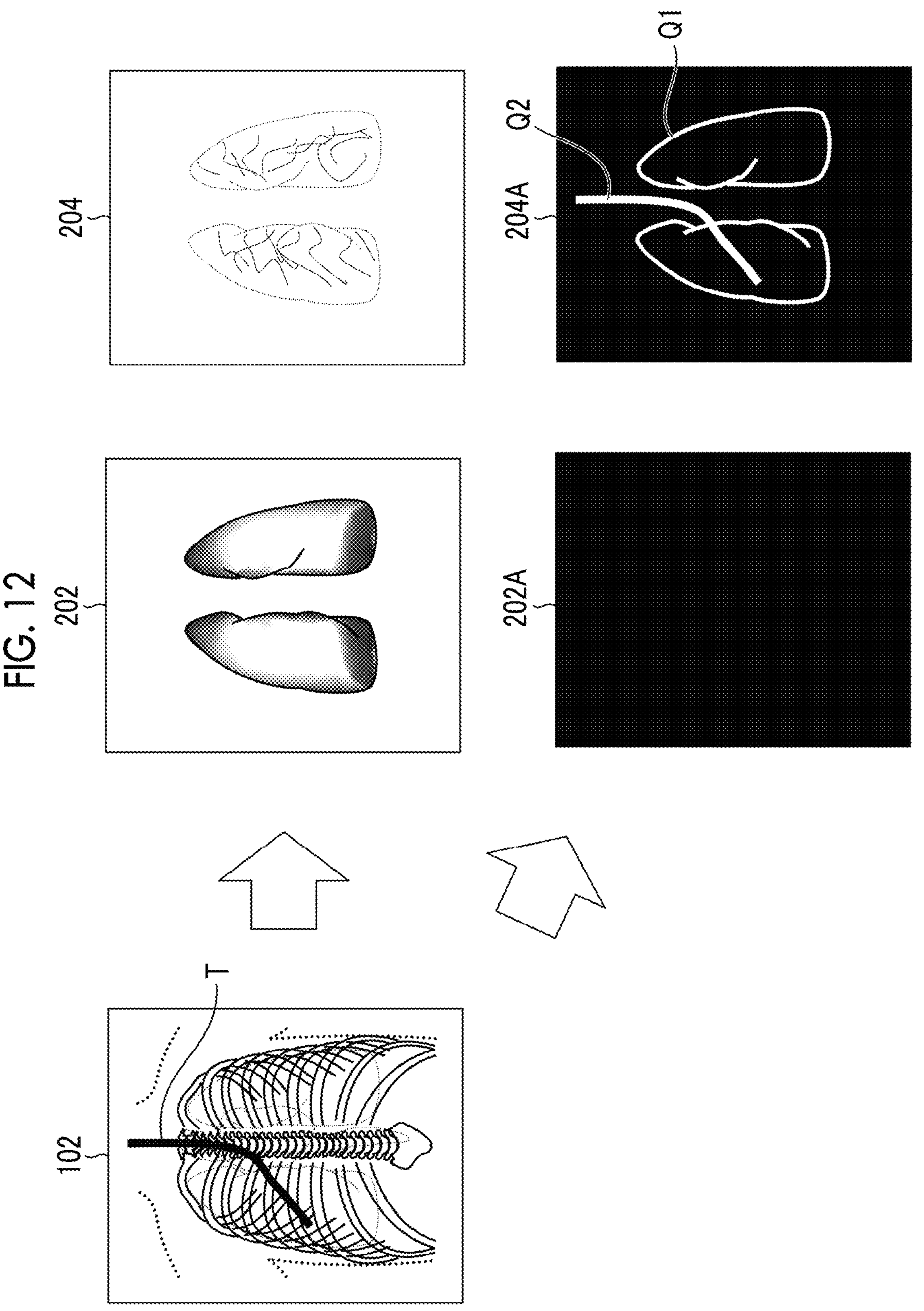
FIG. 12 is a diagram illustrating conversion in a first converter.

FIG. 12 is a diagram illustrating a case in which the first converter 16 converts the simple X-ray image 102 into a first shape feature 202 and a first texture feature 204.

The simple X-ray image 102 obtained by imaging the chest of the human body in a state in which a surgical tool T is inserted is input to the first converter 16. Then, the first converter 16 converts the simple X-ray image 102 into the first shape feature 202 and the first texture feature 204. In the case illustrated in FIG. 12, the first converter 16 converts the simple X-ray image 102 into the first shape feature 202 of a lung shape indicated by thickness information of the lungs. Further, in the case illustrated in FIG. 12, the first converter 16 converts the simple X-ray image 102 into the first texture feature 204 of a lung texture indicated by blood vessels in the lungs.

Furthermore, in the case illustrated in FIG. 12, the first converter 16 outputs a first shape feature reliability 202A ((1-1)-th reliability) and a first texture feature reliability 204A ((1-2)-th reliability). In addition, in FIG. 12, a black portion indicates a portion having a high reliability, and a white portion indicates a portion having a low reliability. The first shape feature reliability 202A has a high reliability as a whole since the shape feature is indicated by information related to the thickness of the lungs. On the other hand, in the first texture feature reliability 204A, since the lung texture indicated by the blood vessels in the lungs is shown, a portion in which the blood vessels are not capable of being detected well has a low reliability. Specifically, in the first texture feature reliability 204A, since fine blood vessels are not capable of being detected in the vicinity of the pleura Q1, the vicinity of the pleura Q1 has a low reliability. In addition, since the blood vessels overlapping the surgical tool T are not capable of being detected, a portion Q2 overlapping the surgical tool T has a low reliability. Further, the reliability may be calculated for each pixel or may be calculated for each predetermined region.

In addition, the conversion by the first converter 16 has been described in FIG. 12. However, similarly, the three-dimensional X-ray CT image 106 is input to the second converter 18, and the second converter 18 outputs a second shape feature 206 (FIG. 13) and a second texture feature 208 (see FIG. 13). Further, similarly to the first converter 16, the second converter 18 outputs a second shape feature reliability 206A ((2-1)-th reliability) and a second texture feature reliability 208A ((2-2)-th reliability).

Furthermore, a case in which the first shape feature reliability 202A (second shape feature reliability 206A) and the first texture feature reliability 204A (second texture feature reliability 208A) are output has been described with reference to FIG. 12. However, these reliabilities may not be output.

First Example of Second Embodiment

Figure 13:
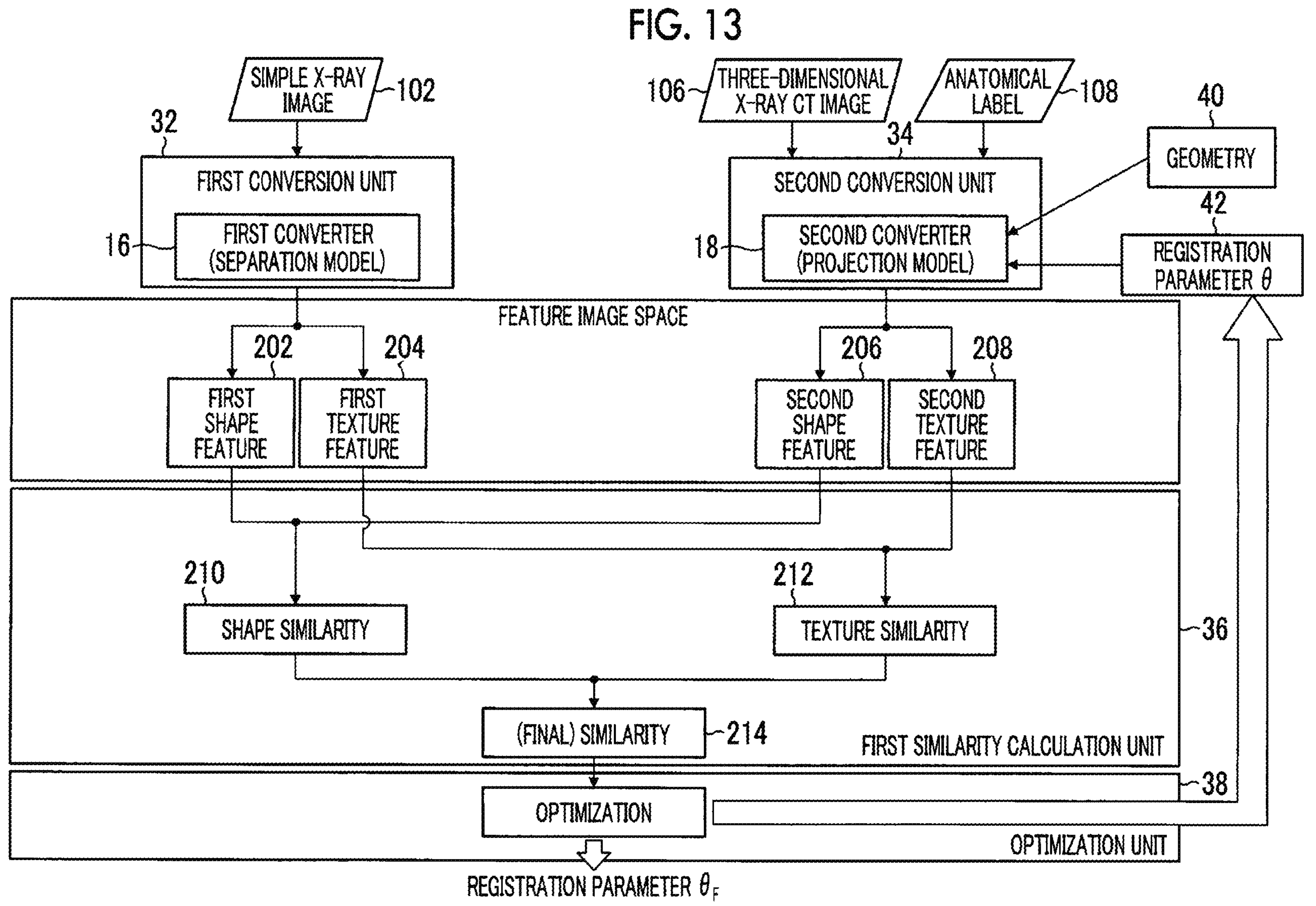
FIG. 13 is a diagram illustrating a first example.

FIG. 13 is a diagram illustrating a first example of the second embodiment. In addition, FIG. 13 is a diagram in which the image acquisition unit 30 of FIG. 2 is omitted. In FIG. 13, the portions that have already been described are denoted by the same reference numerals, and the description thereof will not be repeated.

The first converter 16 receives the simple X-ray image 102 as an input and converts the simple X-ray image 102 into the first shape feature 202 and the first texture feature 204. Here, the first shape feature 202 is an image in the third image space characterized by the region of interest and has information related to the shape feature of the region of interest in the simple X-ray image 102. In addition, the first texture feature 204 is an image in the third image space characterized by the region of interest and has information related to the texture feature of the region of interest in the simple X-ray image 102.

Specifically, the first converter 16 converts the simple X-ray image 102 into the first shape feature 202 which is an image in the feature image space (third image space) characterized by the shape feature of the anatomical region of interest (lung) (see FIG. 12).

In addition, the first converter 16 converts the simple X-ray image 102 into the first texture feature 204 which is an image in the feature image space (third image space) characterized by the texture feature of the anatomical region of interest (lung) (see FIG. 12).

The second converter 18 converts the three-dimensional X-ray CT image 106 into the second shape feature 206 and the second texture feature 208. Here, the second shape feature 206 is an image in the third image space characterized by the region of interest and has information related to the shape feature of the region of interest in the three-dimensional X-ray CT image 106. The second texture feature 208 is an image in the third image space characterized by the region of interest and has information related to the texture feature of the region of interest in the three-dimensional X-ray CT image 106.

The first similarity calculation unit 36 performs the first similarity calculation process to calculate the similarity between the shape features and the similarity between the texture features converted by the first conversion process and the second conversion process. Specifically, the first similarity calculation unit 36 calculates a shape similarity 210 ((1-1)-th similarity) which is a similarity between the first shape feature 202 and the second shape feature 206. Further, the first similarity calculation unit 36 calculates a texture similarity 212 ((1-2)-th similarity) which is a similarity between the first texture feature 204 and the second texture feature 208. Then, the first similarity calculation unit 36 calculates a final similarity 214 (first similarity) from the shape similarity 210 and the texture similarity 212. In addition, since the calculation of the similarity has already been described in the first embodiment, the description thereof will not be repeated here.

In a case in which the final similarity is calculated by the first similarity calculation unit 36, the final similarity 214 is input to the optimization unit 38 as described in the first embodiment. The optimization unit 38 optimizes the registration parameter θ on the basis of the final similarity calculated by the first similarity calculation unit 36. The optimization unit 38 updates the registration parameter θ to calculate the registration parameter $\theta_F$ that maximizes the final similarity, using an optimization algorithm. This optimization of the registration parameter θ by the optimization unit 38 makes it possible to automatically adjust the trade-off between the shape feature and the texture feature and to obtain a similarity with high accuracy and high robustness.

As described above, in this example, the first converter 16 converts the simple X-ray image 102 into the first shape feature 202 and the first texture feature 204, and the second converter 18 converts the three-dimensional X-ray CT image 106 into the second shape feature 206 and the second texture feature 208. Then, the first similarity calculation unit 36 calculates the shape similarity 210 from the first shape feature 202 and the second shape feature 206 and calculates the texture similarity 212 from the first texture feature 204 and the second texture feature 208. Then, the first similarity calculation unit 36 calculates the final similarity. The optimization unit 38 updates the registration parameter θ such that the final similarity is maximized. Therefore, it is possible to automatically adjust the trade-off between the shape feature and the texture feature and to obtain a similarity with high accuracy and high robustness.

In addition, in this embodiment, as in the first embodiment, since the similarity is not automatically designed by metric learning, it is possible to provide the similarity that can be interpreted by humans.

Second Example of Second Embodiment

Next, a second example of the second embodiment will be described. In this example, the first converter 16 further outputs the reliability of the first shape feature 202 and the reliability of the first texture feature 204.

FIG. 14 is a diagram illustrating the second example of the second embodiment. In addition, the portions already described in FIG. 13 are denoted by the same reference numerals, and the description thereof will not be repeated.

In this example, the first converter 16 converts the simple X-ray image 102 into the first shape feature 202 and calculates the first shape feature reliability 202A. Here, the first shape feature reliability 202A is information indicating the reliability of the first shape feature 202. Further, the first converter 16 converts the simple X-ray image 102 into the first texture feature 204 and calculates the first texture feature reliability 204A. Here, the first texture feature reliability 204A is information indicating the calculated reliability of the first texture feature 204.

In a case in which the shape similarity 210 is calculated, the first similarity calculation unit 36 weights the first shape feature 202 on the basis of the first shape feature reliability 202A and calculates the shape similarity 210. Further, in a case in which the texture similarity 212 is calculated, the first similarity calculation unit 36 weights the first texture feature 204 on the basis of the first texture feature reliability 204A and calculates the texture similarity 212. As described above, the first similarity calculation unit 36 performs weighting on the basis of the first shape feature reliability 202A and the first texture feature reliability 204A and calculates the shape similarity 210 and the texture similarity 212. Therefore, in this example, even in a case in which the reliability of the conversion of the simple X-ray image 102 into the first shape feature 202 and the first texture feature 204 by the first converter 16 is low, it is possible to accurately calculate the final similarity 214. In addition, the first similarity calculation unit 36 may select the shape similarity 210 and the texture similarity 212 on the basis of the first shape feature reliability 202A and the first texture feature reliability 204A.

Third Example of Second Embodiment

Next, a third example of the second embodiment will be described. In this example, the first converter 16 further outputs the reliability of the first shape feature 202 and the reliability of the first texture feature 204, and the second converter 18 further outputs the reliability of the second shape feature 206 and the reliability of the second texture feature 208.

FIG. 15 is a diagram illustrating the third example of the second embodiment. In addition, the portions already described in FIGS. 13 and 14 are denoted by the same reference numerals, and the description thereof will not be repeated.

In this example, the first converter 16 converts the simple X-ray image 102 into the first shape feature 202 and calculates the first shape feature reliability 202A. Further, the first converter 16 converts the simple X-ray image 102 into the first texture feature 204 and calculates the first texture feature reliability 204A.

The second converter 18 converts the three-dimensional X-ray CT image 106 into the second shape feature 206 and calculates the second shape feature reliability 206A. Further, the second converter 18 converts the three-dimensional X-ray CT image 106 into the second texture feature 208 and calculates the second texture feature reliability 208A.

In a case in which the shape similarity 210 is calculated, the first similarity calculation unit 36 weights the first shape feature 202 on the basis of the first shape feature reliability 202A, weights the second shape feature 206 on the basis of the second shape feature reliability 206A, and calculates the shape similarity 210. Further, in a case in which the texture similarity 212 is calculated, the first similarity calculation unit 36 weights the first texture feature 204 on the basis of the first texture feature reliability 204A, weights the second texture feature 208 on the basis of the second texture feature reliability 208A, and calculates the texture similarity 212.

As described above, the first similarity calculation unit 36 performs weighting on the basis of the first shape feature reliability 202A, the first texture feature reliability 204A, the second shape feature reliability 206A, and the second texture feature reliability 208A and calculates the shape similarity 210 and the texture similarity 212. Therefore, in this example, even in a case in which the reliability of the conversion by the first converter 16 and the reliability of the conversion by the second converter 18 are significantly different from each other, it is possible to accurately calculate the final similarity 214.

Fourth Example of Second Embodiment

Next, a fourth example of the second embodiment will be described. In this example, the first converter 16 further outputs the reliability of the first shape feature 202 and the reliability of the first texture feature 204, and the second converter 18 further outputs the reliability of the second shape feature 206 and the reliability of the second texture feature 208.

Figure 16:
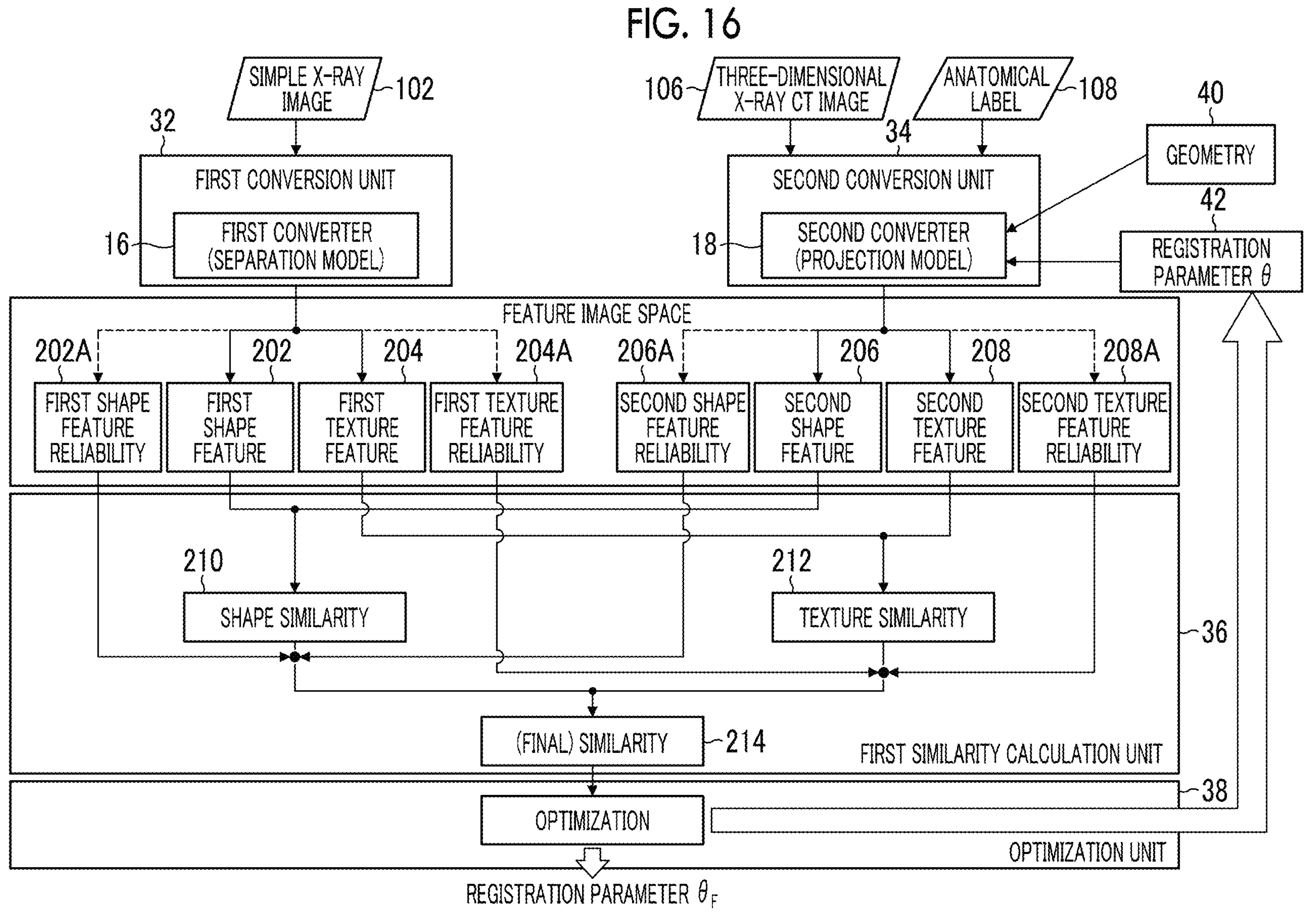
FIG. 16 is a diagram illustrating a fourth example.

FIG. 16 is a diagram illustrating the fourth example of the second embodiment. In addition, the portions already described in FIGS. 13 to 15 are denoted by the same reference numerals, and the description thereof will not be repeated.

In the example, the first converter 16 converts the simple X-ray image 102 into the first shape feature 202 and the first texture feature 204. Further, the first converter 16 outputs the first shape feature reliability 202A and the first texture feature reliability 204A. The second converter 18 converts the three-dimensional X-ray CT image 106 into the second shape feature 206 and the second texture feature 208. Further, the second converter 18 outputs the second shape feature reliability 206A and the second texture feature reliability 208A.

The first similarity calculation unit 36 selects, as the final similarity, the shape similarity 210 or the texture similarity 212 on the basis of the first shape feature reliability 202A, the first texture feature reliability 204A, the second shape feature reliability 206A, and the second texture feature reliability 208A. Specifically, the first similarity calculation unit 36 compares the first shape feature reliability 202A and the second shape feature reliability 206A with the first texture feature reliability 204A and the second texture feature reliability 208A, selects the shape similarity 210 in a case in which the first shape feature reliability 202A and the second shape feature reliability 206A are higher, and selects the texture similarity 212 in a case in which the first texture feature reliability 204A and the second texture feature reliability 208A are higher.

As described above, the first similarity calculation unit 36 selects the shape similarity 210 or the texture similarity 212 as the final similarity on the basis of the first shape feature reliability 202A, the first texture feature reliability 204A, the second shape feature reliability 206A, and the second texture feature reliability 208A. Therefore, it is possible to calculate the final similarity on the basis of the shape similarity 210 or the texture similarity 212 having a higher reliability.

Modification Example 1 of Second Embodiment

Next, Modification Example 1 of the second embodiment will be described. In the above-described example, the case in which the first shape feature 202 is a lung shape has been described. However, a first shape feature 220 according to this example is a shape of bronchi.

Figure 17:
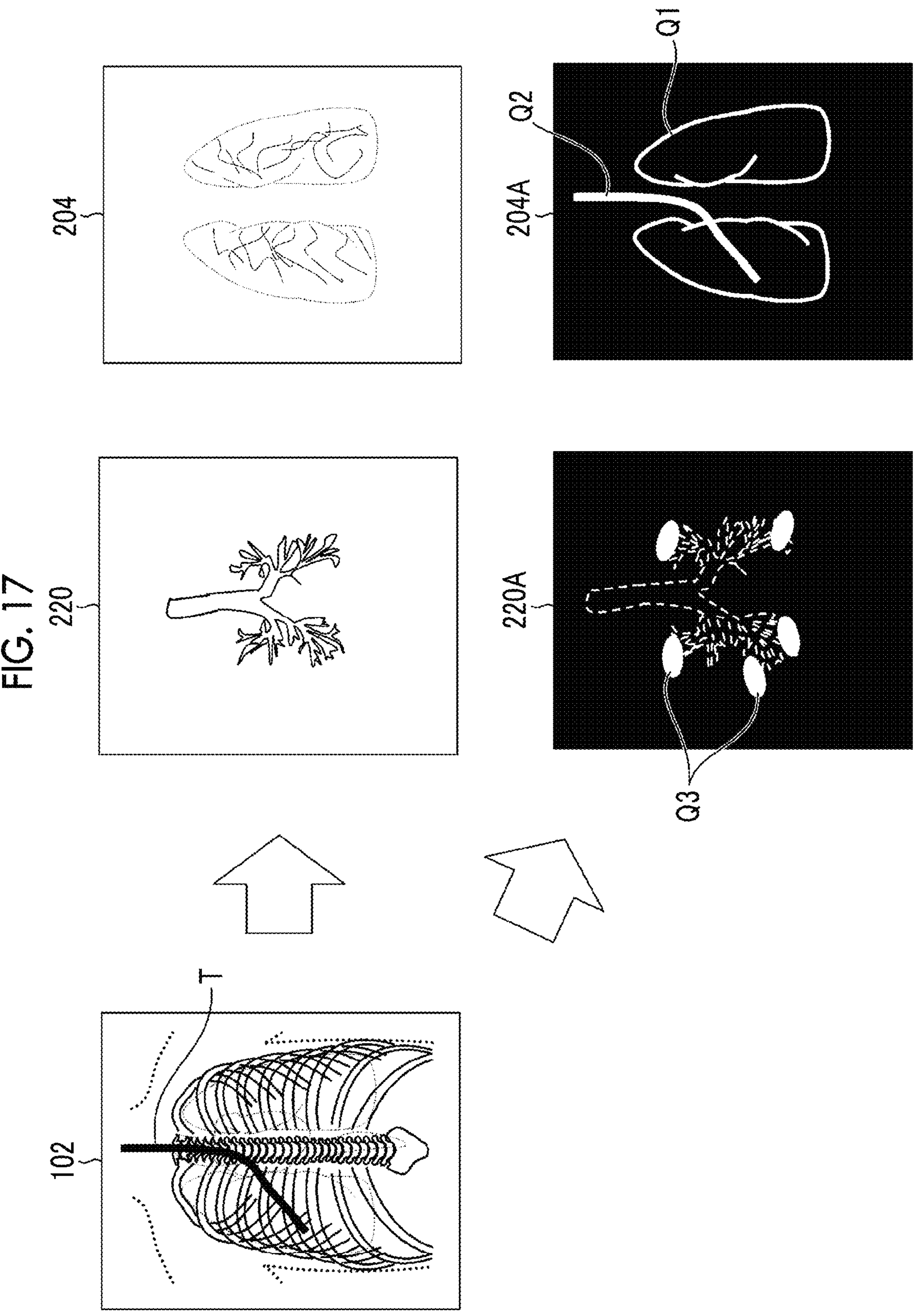
FIG. 17 is a diagram illustrating the conversion in the first converter.

FIG. 17 is a diagram illustrating a case in which the first converter 16 converts the simple X-ray image 102 into the first shape feature 220 and the first texture feature 204. In addition, the portions already described in FIG. 12 are denoted by the same reference numerals, and the description thereof will not be repeated. Further, in FIG. 17, only the first converter 16 will be described. However, similarly, the second converter 18 converts the three-dimensional X-ray CT image 106 into the second shape feature 206 and the second texture feature 208 to correspond to the first converter 16.

The simple X-ray image 102 obtained by imaging the chest of the human body is input to the first converter 16. Then, the first converter 16 converts the simple X-ray image 102 into the first shape feature 220 and the first texture feature 204. In the case illustrated in FIG. 17, the first converter 16 converts the simple X-ray image 102 into the first shape feature 220 having information related to the shape of the bronchi. Further, in the case illustrated in FIG. 17, the first converter 16 converts the simple X-ray image 102 into the first texture feature 204 of the lung texture indicated by the blood vessels in the lungs.

Furthermore, in the case illustrated in FIG. 17, the first converter 16 outputs a first shape feature reliability 220A and the first texture feature reliability 204A. Moreover, in the case illustrated in FIG. 17, a black portion indicates a portion with a high reliability, and a white portion indicates a portion with a low reliability. In addition, a white dotted line indicates a shape.

In the first shape feature reliability 220A, a portion in which the shape of a part other than a peripheral part Q3 of the bronchus can be sufficiently detected has a high reliability. On the other hand, in the first shape feature reliability 220A, since blood vessels are not capable of being detected well in the peripheral part Q3 of the bronchus, the peripheral part Q3 has a low reliability. Therefore, in the simple X-ray image 102, a portion in which the shape of the bronchi is visible has a high reliability, and registration is directly performed. In addition, the surgical tool T has restrictions on passing through the bronchus. Therefore, it is considered that uncertainty is not increased even in a case in which the bronchus and the surgical tool T overlap each other. On the other hand, the peripheral part of the bronchus is not capable of being detected well from the simple X-ray image 102. Therefore, registration is indirectly performed on a peripheral part of the bronchus by the running of the blood vessels.

As described above, in this example, registration is performed on the basis of the similarity between the shape feature of the shape of the bronchi and the lung texture. Therefore, it is possible to obtain a similarity with high accuracy and high robustness.

Modification Example 2 of Second Embodiment

Next, Modification Example 2 of the second embodiment will be described. In the above-described example, the registration is performed by calculating the similarity between the shape feature and the texture feature. In this example, the registration is performed by calculating a similarity between an anatomical region and a disease region.

Figure 18:
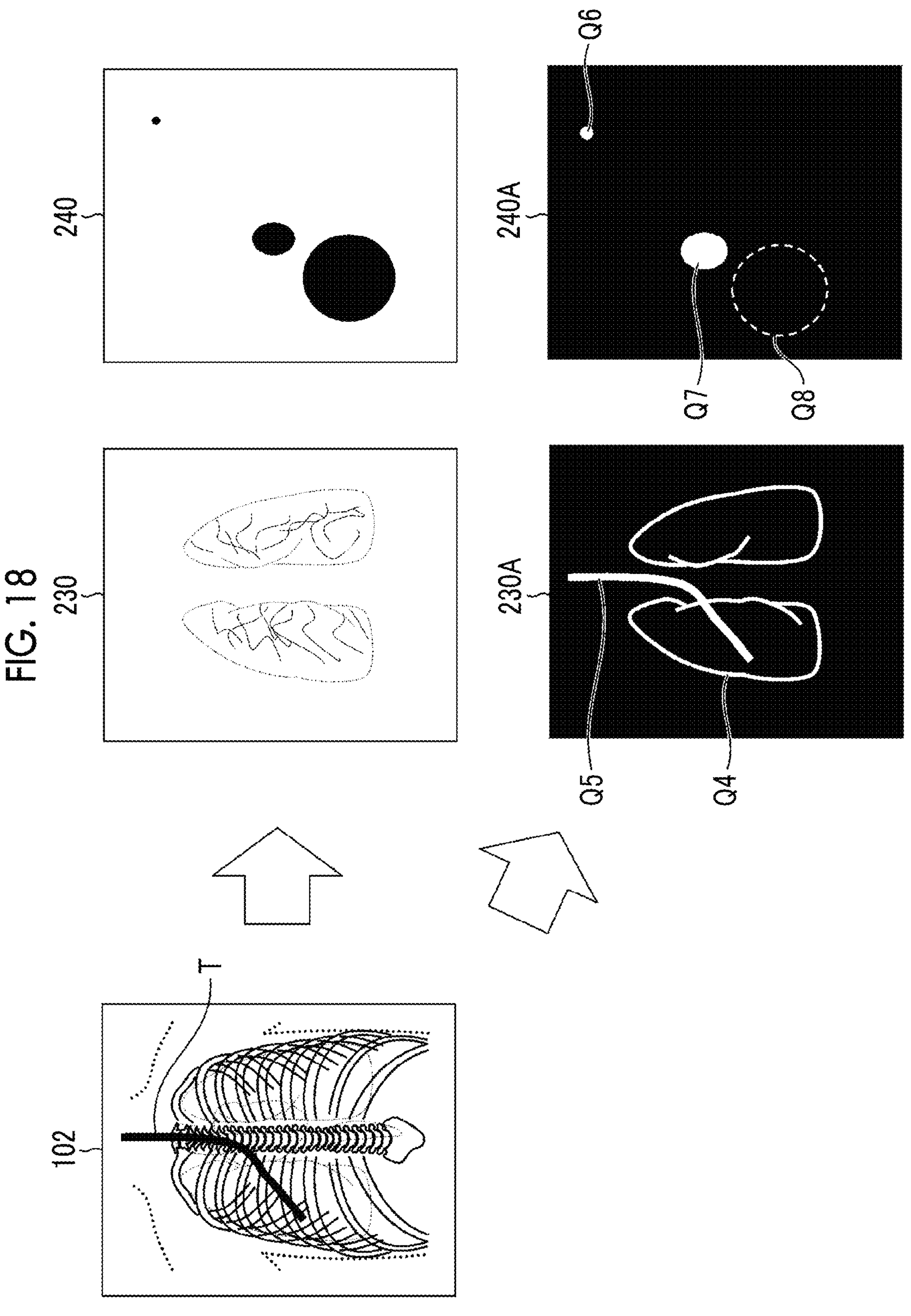
FIG. 18 is a diagram illustrating the conversion in the first converter.

FIG. 18 is a diagram illustrating a case in which the first converter 16 converts the simple X-ray image 102 into a first anatomical region 230 and a first disease region 240. In addition, in FIG. 18, only the first converter 16 will be described. However, similarly, the second converter 18 converts the three-dimensional X-ray CT image 106 into a second anatomical region and a second disease region to correspond to the first converter 16.

The first converter 16 receives the simple X-ray image 102 obtained by imaging the chest of the human body as an input and converts the simple X-ray image 102 into the first anatomical region 230 and the first disease region 240. In the case illustrated in FIG. 18, the first converter 16 converts the simple X-ray image 102 into the first anatomical region 230 related to the blood vessels in the lungs. Further, in the case illustrated in FIG. 18, the first converter 16 converts the simple X-ray image 102 into the first disease region 240 related to lung nodules. Moreover, the second converter 18 converts the three-dimensional X-ray CT image 106 into the second anatomical region and the second disease region.

In addition, in the case illustrated in FIG. 18, the first converter 16 outputs a first anatomical region reliability 230A ((1-1)-th reliability) indicating the reliability of the first anatomical region 230 and a first disease region reliability 240A ((1-2)-th reliability) indicating the reliability of the first disease region 240. Further, the second converter 18 outputs a second anatomical region reliability ((2-1)-th reliability) indicating the reliability of the second anatomical region and a second disease region reliability ((2-2)-th reliability) indicating the reliability of the second disease region. Furthermore, in the case illustrated in FIG. 18, a black portion indicates a portion having a high reliability, and a white portion indicates a portion having a low reliability. In addition, a white dotted line indicates a shape.

Since the first anatomical region reliability 230A is indicated by the anatomical region of the blood vessels running in the lungs, a portion in which the blood vessels are not capable of being detected well has a low reliability. Specifically, in the first anatomical region reliability 230A, since fine blood vessels are not capable of being detected in the vicinity of the pleura Q4, the vicinity of the pleura Q4 has a low reliability. In addition, in the first anatomical region reliability 230A, since the blood vessel overlapping the surgical tool T is not capable of being detected, a portion Q5 overlapping the surgical tool T has a low reliability. In the first disease region reliability 240A, a large nodule (see reference numeral Q8) has a high reliability, and a minute nodule or a nodule overlapping a bone or a hilum of the lung has a low reliability (see reference numerals Q6 and Q7). In this case, the registration is indirectly performed for the small nodule having a low reliability or the nodule overlapping the bone or the hilum of the lung due to the running of the blood vessels (with reference to the first anatomical region and the second anatomical region) and is directly performed for the nodule having a large reliability (with reference to the first disease region and the second disease region).

The first similarity calculation unit 36 performs the first similarity calculation process to calculate the similarity between the anatomical regions converted by the first conversion process and the similarity between the disease regions converted by the second conversion process. Specifically, the first similarity calculation unit 36 calculates an anatomical region similarity ((1-1)-th similarity) which is a similarity between the first anatomical region 230 and the second anatomical region. In addition, the first similarity calculation unit 36 calculates a disease region similarity ((1-2)-th similarity) which is a similarity between the first disease region 240 and the second disease region. The first similarity calculation unit 36 calculates the final similarity (first similarity) from the anatomical region similarity and the disease region similarity. In addition, since the calculation of the similarity has already been described in the first embodiment, the description thereof will not be repeated here. Further, the first similarity calculation unit 36 may calculate the anatomical region similarity and the disease region similarity on the basis of the first anatomical region reliability 230A and the first disease region reliability 240A and calculate the final similarity. For example, the first similarity calculation unit 36 may weight the anatomical region similarity and the disease region similarity on the basis of the first anatomical region reliability 230A and the first disease region reliability 240A and calculate the final similarity. Furthermore, for example, the first similarity calculation unit 36 may select the anatomical region similarity or the disease region similarity on the basis of the anatomical region reliability 230A and the first disease region reliability 240A and calculate the final similarity. The first similarity calculation unit 36 may calculate the anatomical region similarity and the disease region similarity on the basis of the first anatomical region reliability 230A, the first disease region reliability 240A, the second anatomical region reliability, and the second disease region reliability and calculate the final similarity. For example, the first similarity calculation unit 36 may weight the anatomical region similarity on the basis of the first anatomical region reliability 230A and the second anatomical region reliability and may weight the disease region similarity on the basis of the first disease region reliability 240A and the second disease region reliability to calculate the final similarity. In addition, for example, the first similarity calculation unit 36 may select the anatomical region similarity or the disease region similarity on the basis of the first anatomical region reliability 230A, the first disease region reliability 240A, the second anatomical region reliability, and the second disease region reliability and calculate the final similarity.

As described above, in this example, the registration is performed on the basis of the similarity between the anatomical region and the disease region. Therefore, it is possible to obtain a similarity with high accuracy and high robustness.

In the above-described embodiments, a hardware structure of a processing unit that executes various processes is the following various processors. The various processors include, for example, a central processing unit (CPU) which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of these various processors or by two or more processors of the same type or different types (for example, a plurality of FPGAs or a combination of a CPU and an FPGA). Moreover, a plurality of processing units may be configured by one processor. A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured by using one or more of the various processors as a hardware structure.

In addition, specifically, an electric circuit (circuitry) obtained by combining circuit elements, such as semiconductor elements, can be used as the hardware structure of the various processors.

Each of the above-described configurations and functions can be implemented by any hardware, software, or a combination thereof as appropriate. For example, the present invention can be also applied to a program that causes a computer to execute the above-described processing steps (processing procedures), a computer-readable recording medium (non-transitory recording medium) having the program recorded thereon, or a computer in which the program can be installed.

The examples of the present invention have been described above. However, it is needless to say that the present invention is not limited to the above-described embodiments and various modifications can be made without departing from the gist of the present invention.

EXPLANATION OF REFERENCES

10: image processing device
12: processor
14: memory
16: first converter
18: second converter
20: display unit
22: input/output interface
24: operation unit
30: image acquisition unit
32: first conversion unit
34: second conversion unit
36: first similarity calculation unit
38: optimization unit
40: geometry
102: simple X-ray image
106: three-dimensional X-ray CT image
108: anatomical label

What is claimed is:

1. An image processing device comprising:
a processor,
wherein the processor is configured to execute:
an image acquisition process of acquiring a first image in a first image space and a second image in a second image space different from the first image space, wherein the first image and the second image are images of a same patient;

a first conversion process of converting the first image into an image in a third image space that is characterized by a region of interest, using a first converter;

a second conversion process of converting the second image into an image in the third image space, using a second converter; and a first similarity calculation process of calculating a first similarity between the first image and the second image in the third image space, wherein the first converter converts the first image into a first shape feature and a first texture feature, the second converter converts the second image into a second shape feature and a second texture feature, and in the first similarity calculation process, the first similarity is calculated on the basis of a similarity between the first shape feature and the second shape feature and a similarity between the first texture feature and the second texture feature.

2. The image processing device according to claim 1, wherein, in the first conversion process, the first image is converted into images in a plurality of the third image spaces, in the second conversion process, the second image is converted into images in the plurality of third image spaces to correspond to the first conversion process, and in the first similarity calculation process, the first similarity in each of the plurality of third image spaces is calculated, and a plurality of the calculated first similarities are integrated.

3. The image processing device according to claim 2, wherein, in the first conversion process, the first image is converted by at least two or more first converters into images in the third image spaces which correspond to each of the first converters, and in the second conversion process, the second image is converted by at least two or more second converters into images in the third image spaces, which correspond to each of the second converters, to correspond to the first conversion process.

4. The image processing device according to claim 2, wherein, in the first similarity calculation process, the first similarity is calculated for each of the plurality of third image spaces.

5. The image processing device according to claim 1, wherein the region of interest is an anatomical region of interest, and the third image space is a feature image space that is characterized by the anatomical region of interest.

6. The image processing device according to claim 1, wherein the processor is configured to:

execute a region-of-interest receiving process of receiving an input of the region of interest, the first converter converts the first image on the third image space characterized by the region of interest received in the region-of-interest receiving process, and the second converter converts the second image on the third image space characterized by the region of interest received in the region-of-interest receiving process.

7. The image processing device according to claim 1, wherein the first converter outputs a first reliability indicating a reliability of the image after the conversion, and in the first similarity calculation process, the first similarity that has a weight or is to be selected is calculated on the basis of the first reliability.

8. The image processing device according to claim 7, wherein the first converter outputs the first reliability for each pixel of the image after the conversion.

9. The image processing device according to claim 1, wherein the first converter outputs a first reliability indicating a reliability of the image after the conversion, the second converter outputs a second reliability indicating a reliability of the image after the conversion, and in the first similarity calculation process, the first similarity having a weight is calculated on the basis of the first reliability and the second reliability.

10. The image processing device according to claim 9, wherein the first converter outputs the first reliability for each pixel of the image after the conversion, and the second converter outputs the second reliability for each pixel of the image after the conversion.

11. The image processing device according to claim 1, wherein the first converter outputs a (1-1)-th reliability indicating a reliability of the first shape feature and outputs a (1-2)-th reliability indicating a reliability of the first texture feature, and in the first similarity calculation process, a (1-1)-th similarity between the first shape feature and the second shape feature and a (1-2)-th similarity between the first texture feature and the second texture feature are calculated on the basis of the (1-1)-th reliability and the (1-2)-th reliability, and the first similarity is calculated.

12. The image processing device according to claim 11, wherein, in the first similarity calculation process, the (1-1)-th similarity and the (1-2)-th similarity are weighted on the basis of the (1-1)-th reliability and the (1-2)-th reliability, and the first similarity is calculated.

13. The image processing device according to claim 11, wherein, in the first similarity calculation process, the (1-1)-th similarity or the (1-2)-th similarity is selected on the basis of the (1-1)-th reliability and the (1-2)-th reliability, and the first similarity is calculated.

14. The image processing device according to claim 1, wherein the first converter outputs a (1-1)-th reliability indicating a reliability of the first shape feature and outputs a (1-2)-th reliability indicating a reliability of the first texture feature, the second converter outputs a (2-1)-th reliability indicating a reliability of the second shape feature and outputs a (2-2)-th reliability indicating a reliability of the second texture feature, and in the first similarity calculation process, a (1-1)-th similarity between the first shape feature and the second shape feature and a (1-2)-th similarity between the first texture feature and the second texture feature are calculated on the basis of the (1-1)-th reliability, the (1-2)-th reliability, the (2-1)-th reliability, and the (2-2)-th reliability, and the first similarity is calculated.

15. The image processing device according to claim 14, wherein, in the first similarity calculation process, the (1-1)-th similarity is weighted on the basis of the (1-1)-th reliability and the (2-1)-th reliability, the (1-2)-th similarity is weighted on the basis of the (1-2)-th reliability and the (2-2)-th reliability, and the first similarity is calculated.

16. The image processing device according to claim 14, wherein, in the first similarity calculation process, the (1-1)-th similarity or the (1-2)-th similarity is selected on the basis of the (1-1)-th reliability, the (1-2)-th reliability, the (2-1)-th reliability, and the (2-2)-th reliability, and the first similarity is calculated.

17. The image processing device according to claim 1, wherein the processor is configured to:

execute a second similarity calculation process of calculating a second similarity between the first image and the second image, and in the first similarity calculation process, the first similarity weighted on the basis of the second similarity is calculated.

18. The image processing device according to claim 17, wherein the second similarity is an amount of mutual information between a simple X-ray image and a pseudo X-ray image generated from a three-dimensional X-ray CT image.

19. The image processing device according to claim 17, wherein the second similarity is a gradient correlation between a simple X-ray image and a pseudo X-ray image generated from a three-dimensional X-ray CT image.

20. The image processing device according to claim 1, wherein a registration parameter between the first image and the second image is input to the second converter, and the processor is configured to:

execute an optimization process of updating the registration parameter on the basis of the first similarity.

21. The image processing device according to claim 1, wherein the first image is a simple X-ray image, and the second image is a three-dimensional X-ray CT image.

22. The image processing device according to claim 21, wherein the second converter converts the three-dimensional X-ray CT image into an image obtained by correcting an attenuation value of the second image in a projection plane.

23. The image processing device according to claim 22, wherein the first converter converts the simple X-ray image on a two-dimensional feature image space with a model constructed using machine learning, and the second converter converts the three-dimensional X-ray CT image into the image obtained by correcting the attenuation value in the projection plane by masking a label of the region of interest on the three-dimensional X-ray CT image and projecting the masked three-dimensional X-ray CT image onto the two-dimensional feature image space.

24. A correct answer data generation device that generates correct answer data for learning interpretation of a simple X-ray image on the basis of the first similarity obtained by the image processing device according to claim 1.

25. A similar image search device that searches for a similar image on the basis of the first similarity obtained by the image processing device according to claim 1.

26. An image processing device comprising:

a processor, wherein the processor is configured to execute:

an image acquisition process of acquiring a first image in a first image space and a second image in a second image space different from the first image space, wherein the first image and the second image are images of a same patient;

a first conversion process of converting the first image into an image in a third image space that is characterized by a region of interest, using a first converter;

a second conversion process of converting the second image into an image in the third image space, using a second converter; and a first similarity calculation process of calculating a first similarity between the first image and the second image in the third image space, wherein the first converter converts the first image into a first anatomical region and a first disease region, the second converter converts the second image into a second anatomical region and a second disease region, and in the first similarity calculation process, the first similarity is calculated on the basis of a similarity between the first anatomical region and the second anatomical region and a similarity between the first disease region and the second disease region.

27. The image processing device according to claim 26, wherein the first converter outputs a (1-1)-th reliability indicating a reliability of the first anatomical region and outputs a (1-2)-th reliability indicating a reliability of the first disease region, and in the first similarity calculation process, a (1-1)-th similarity between the first anatomical region and the second anatomical region and a (1-2)-th similarity between the first disease region and the second disease region are calculated on the basis of the (1-1)-th reliability and the (1-2)-th reliability, and the first similarity is calculated.

28. The image processing device according to claim 27, wherein, in the first similarity calculation process, the (1-1)-th similarity and the (1-2)-th similarity are weighted on the basis of the (1-1)-th reliability and the (1-2)-th reliability, and the first similarity is calculated.

29. The image processing device according to claim 27, wherein, in the first similarity calculation process, the (1-1)-th similarity or the (1-2)-th similarity is selected on the basis of the (1-1)-th reliability and the (1-2)-th reliability, and the first similarity is calculated.

30. The image processing device according to claim 26, wherein the first converter outputs a (1-1)-th reliability indicating a reliability of the first anatomical region and outputs a (1-2)-th reliability indicating a reliability of the first disease region, the second converter outputs a (2-1)-th reliability indicating a reliability of the second anatomical region and outputs a (2-2)-th reliability indicating a reliability of the second disease region, and in the first similarity calculation process, a (1-1)-th similarity between the first anatomical region and the second anatomical region and a (1-2)-th similarity between the first disease region and the second disease region are calculated on the basis of the (1-1)-th reliability, the (1-2)-th reliability, the (2-1)-th reliability, and the (2-2)-th reliability, and the first similarity is calculated.

31. The image processing device according to claim 30, wherein, in the first similarity calculation process, the (1-1)-th similarity is weighted on the basis of the (1-1)-th reliability and the (2-1)-th reliability, the (1-2)-th similarity is weighted on the basis of the (1-2)-th reliability and the (2-2)-th reliability, and the first similarity is calculated.

32. The image processing device according to claim 30, wherein, in the first similarity calculation process, the (1-1)-th similarity or the (1-2)-th similarity is selected on the basis of the (1-1)-th reliability, the (1-2)-th reliability, the (2-1)-th reliability, and the (2-2)-th reliability, and the first similarity is calculated.

33. An image processing method using an image processing device including a processor, the image processing method comprising:

causing the processor to execute:

an image acquisition step of acquiring a first image in a first image space and a second image in a second image space different from the first image space, wherein the first image and the second image are images of a same patient;

a first conversion step of converting the first image into an image in a third image space that is characterized by a region of interest, using a first converter;

a second conversion step of converting the second image into an image in the third image space using a second converter; and a first similarity calculation step of calculating a first similarity between the first image and the second image in the third image space, wherein the first converter converts the first image into a first shape feature and a first texture feature, the second converter converts the second image into a second shape feature and a second texture feature, and in the first similarity calculation step, the first similarity is calculated on the basis of a similarity between the first shape feature and the second shape feature and a similarity between the first texture feature and the second texture feature.

34. A non-transitory computer-readable recording medium which records thereon a program for causing, when read by a computer, the computer to execute the image processing method according to claim 33.

35. An image processing method using an image processing device including a processor, the image processing method comprising:

causing the processor to execute:

an image acquisition step of acquiring a first image in a first image space and a second image in a second image space different from the first image space, wherein the first image and the second image are images of a same patient;

a first conversion step of converting the first image into an image in a third image space that is characterized by a region of interest, using a first converter;

a second conversion step of converting the second image into an image in the third image space using a second converter; and a first similarity calculation step of calculating a first similarity between the first image and the second image in the third image space, wherein the first converter converts the first image into a first anatomical region and a first disease region, the second converter converts the second image into a second anatomical region and a second disease region, and in the first similarity calculation step, the first similarity is calculated on the basis of a similarity between the first anatomical region and the second anatomical region and a similarity between the first disease region and the second disease region.

36. A non-transitory computer-readable recording medium which records thereon a program for causing, when read by a computer, the computer to execute the image processing method according to claim 35.

* * * * *